US008226889B2

(12) United States Patent
Nakaya

(10) Patent No.: US 8,226,889 B2
(45) Date of Patent: Jul. 24, 2012

(54) SAMPLE PROCESSING SYSTEM

(75) Inventor: Masanori Nakaya, Kobe (JP)

(73) Assignee: Sysmex Corporation, Kobe (JP)

( * ) Notice: Subject to any disclaimer, the term of this patent is extended or adjusted under 35 U.S.C. 154(b) by 309 days.

(21) Appl. No.: 11/998,617

(22) Filed: Nov. 30, 2007

(65) Prior Publication Data

US 2008/0131318 A1    Jun. 5, 2008

(30) Foreign Application Priority Data

Nov. 30, 2006    (JP) .................................. 2006-324442

(51) Int. Cl.
*G01N 15/06*    (2006.01)
*G01N 33/00*    (2006.01)
*G01N 33/48*    (2006.01)

(52) U.S. Cl. .............. 422/63; 422/62; 436/174; 436/43; 436/47

(58) Field of Classification Search .................. 436/174, 436/43, 47; 422/62, 63
See application file for complete search history.

(56) References Cited

U.S. PATENT DOCUMENTS

| 4,675,977 A | | 6/1987 | Kölblin et al. | |
| 5,209,903 A | * | 5/1993 | Kanamori et al. | 422/65 |
| 5,356,596 A | * | 10/1994 | Nokihara et al. | 422/131 |
| 2003/0220761 A1 | * | 11/2003 | Biwa | 702/127 |
| 2005/0214166 A1 | * | 9/2005 | Itoh | 422/65 |
| 2008/0069730 A1 | * | 3/2008 | Itoh | 422/65 |
| 2008/0145939 A1 | * | 6/2008 | Jakubowicz et al. | 436/54 |

FOREIGN PATENT DOCUMENTS

| JP | S60-115867 | 6/1985 |
| JP | H06-51253 | 7/1994 |
| JP | 2001-349897 A | 12/2001 |

* cited by examiner

*Primary Examiner* — Brian J Sines
(74) *Attorney, Agent, or Firm* — Brinks Hofer Gilson & Lione

(57) ABSTRACT

A sample processing system is disclosed that comprising: a first sample processing apparatus; a second sample processing apparatus; a third sample processing apparatus; a first moving mechanism for moving, in a first direction, the second sample processing apparatus and the third sample processing apparatus relative to the first sample processing apparatus; and a second moving mechanism for moving, in a second direction crossing the first direction, at least one among the second sample processing apparatus and the third sample processing apparatus.

18 Claims, 20 Drawing Sheets

SAMPLE PROCESSING SYSTEM

RELATED APPLICATIONS

This application claims priority from Japanese Patent Application 2006-324442 filed on Nov. 30, 2006, the disclosure of which is herein incorporated by reference in its entirety.

FIELD OF THE INVENTION

This invention relates to a sample processing system, and specifically relates to a sample processing system provided with a plurality of sample processing devices installed in a line in a predetermined direction.

BACKGROUND

Large numbers of sample tests are efficiently being performed in recent years by sample processing systems which have a plurality of connected sample processing devices for processing samples. In such sample processing systems, a plurality of sample processing devices are disposed adjacently and connected, and the plurality of sample processing devices are further connected to a conveying device which conveys samples and the like. In such sample processing systems, adequate space is provided between each of the sample processing devices by using a mechanism to separate the sample processing devices to facilitate repair and maintenance of the sample processing devices.

As an example of such a sample processing system, known is a sample processing system which is configured to allow easy repair and maintenance of the plurality of sample processing devices (for example, refer to Japanese Laid-Open Patent Publication No. 2001-349897).

The sample processing system disclosed in Japanese Laid-Open Patent Publication No. 2001-349897 is configured so that one among two adjacent sample processing devices is capable of sliding in a single predetermined direction (horizontal direction). A user can easily perform maintenance and repair of each of the sample processing devices by sliding one sample processing device relative to the other sample processing device so as to separate the two sample processing devices.

In the sample processing system disclosed in Japanese Laid-Open Patent Publication No. 2001-349897, however, the sample processing device can only slide in a single predetermined direction. Therefore, it is difficult to separate the two sample processing devices when there is an obstruction in the direction in which the sample processing device slides. This situation is inconvenient in that it becomes difficult to maintain and repair the sample processing device. A problem therefore arises with the sample processing system disclosed in Japanese Laid-Open Patent Publication No. 2001-349897 insofar as the location of the installation is limited by consideration of the ability of the user to maintain and repair the sample processing devices.

SUMMARY

The scope of the present invention is defined solely by the appended claims, and is not affected to any degree by the statements within this summary.

A first sample processing system embodying features of the present invention includes: a first sample processing apparatus; a second sample processing apparatus; a third sample processing apparatus; a first moving mechanism for moving, in a first direction, the second sample processing apparatus and the third sample processing apparatus relative to the first sample processing apparatus; and a second moving mechanism for moving, in a second direction crossing the first direction, at least one among the second sample processing apparatus and the third sample processing apparatus.

A second sample processing system embodying features of the present invention includes: a first sample processing apparatus; a second sample processing apparatus; a third sample processing apparatus; a first moving mechanism for moving, in a first direction, the second sample processing apparatus and the third sample processing apparatus relative to the first sample processing apparatus; and a second moving mechanism for moving, in a second direction crossing the first direction, the second sample processing apparatus and the third sample processing apparatus.

A third sample processing system embodying features of the present invention includes: a first sample processing apparatus; a second sample processing apparatus; a third sample processing apparatus; a first moving mechanism for moving the second sample processing apparatus in a first direction relative to the first sample processing apparatus; and a second moving mechanism for moving the third sample processing apparatus in a second direction crossing the first direction.

A fourth sample processing system embodying features of the present invention includes: a first sample processing apparatus; a second sample processing apparatus; a first moving mechanism for moving the second sample processing apparatus in a first direction relative to the first sample processing apparatus; and a second moving mechanism for moving the second sample processing apparatus in a second direction crossing the first direction.

DETAILED DESCRIPTION OF THE PREFERRED EMBODIMENTS

The embodiments of the present invention are described hereinafter based on the drawings.

Figure 1:
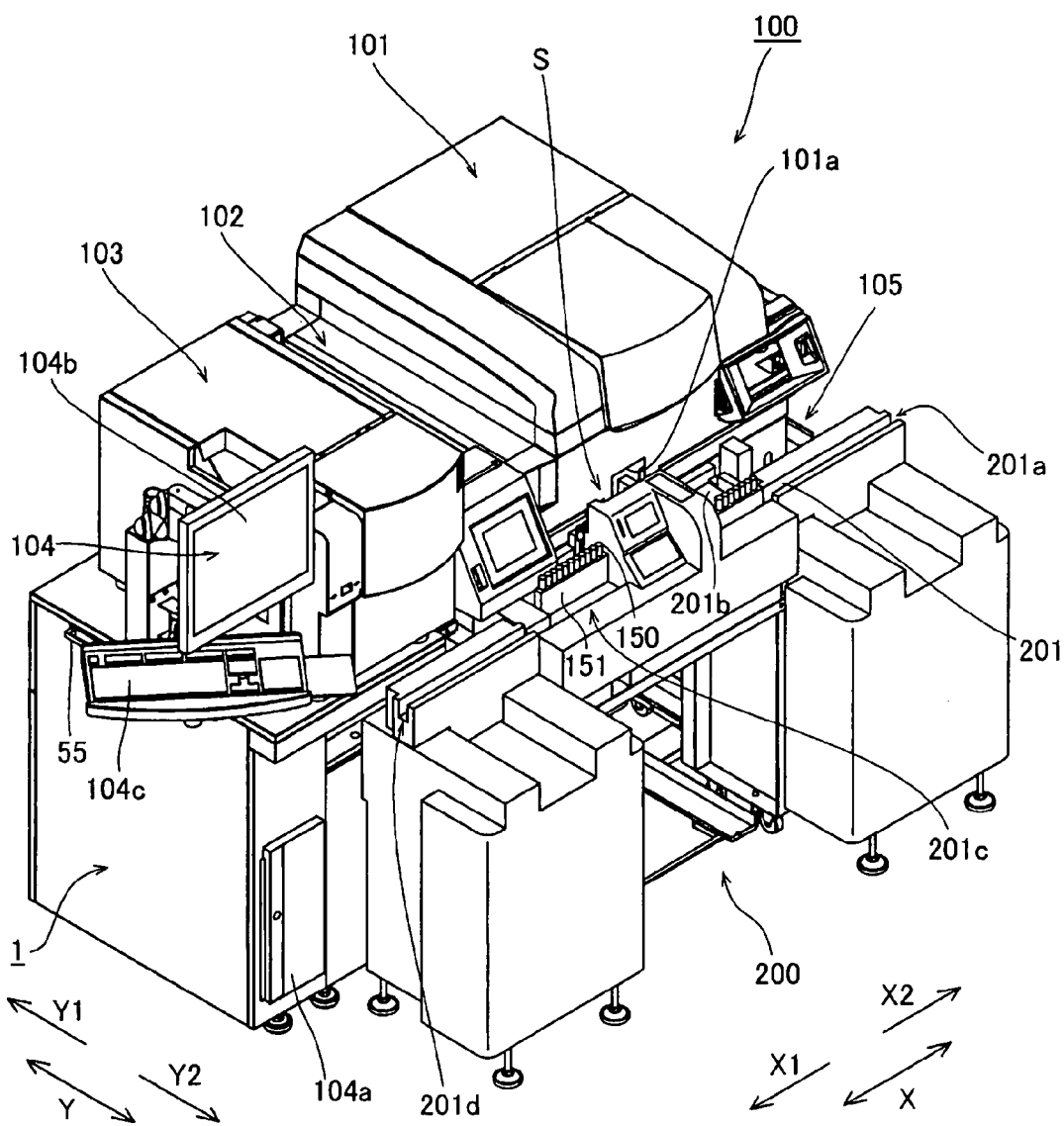
FIG. 1 is a perspective view of the layout of an embodiment of an automatic blood image analyzing system of the present invention during analysis.
Figure 2:
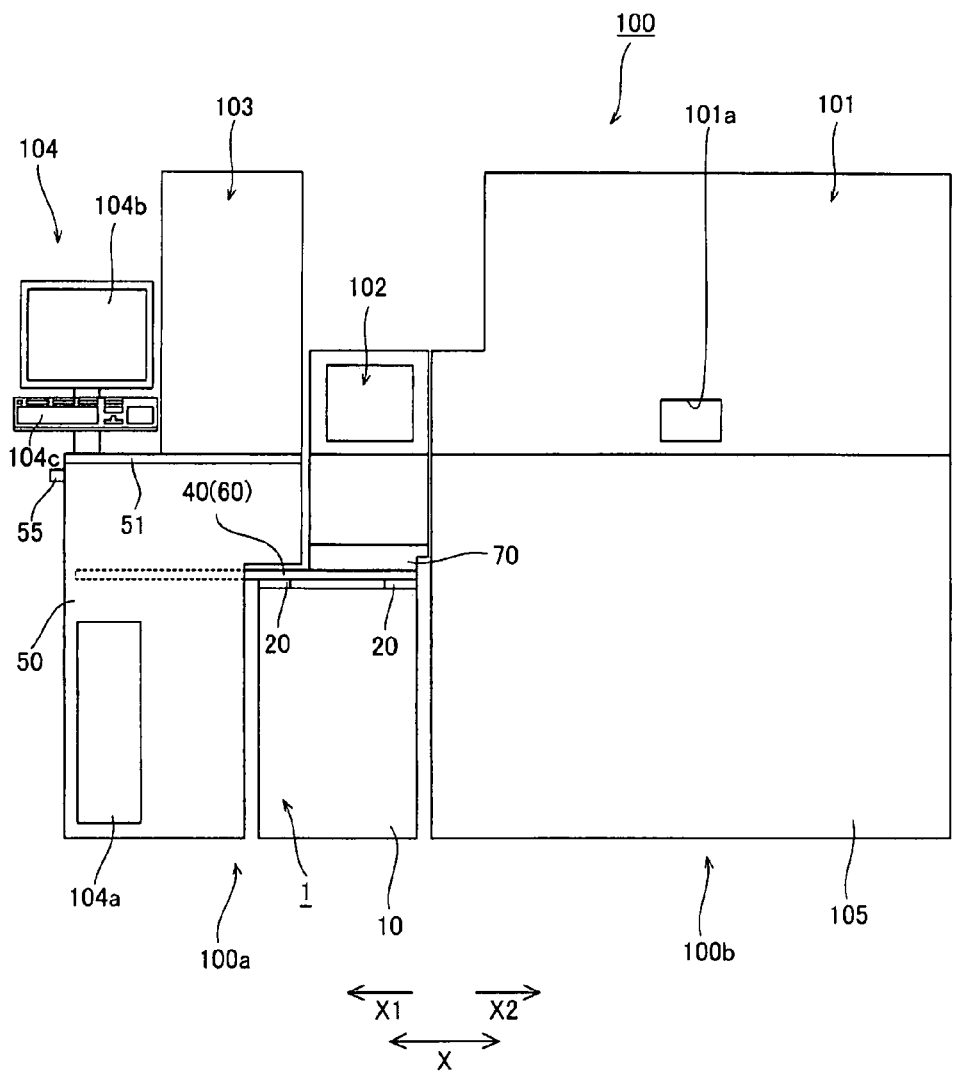
FIG. 2 is a front view schematically showing the automatic blood image analyzer of FIG. 1.
Figure 3:
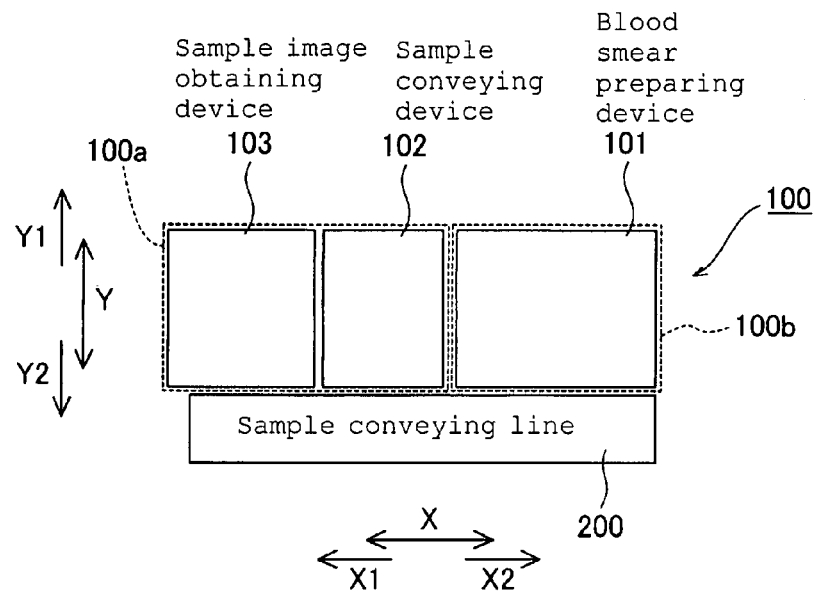
FIG. 3 is a front view schematically showing the automatic blood image analyzer of FIG. 1.

FIG. 2 is a perspective view showing the overall structure of an automatic blood image analyzing system of an embodiment of the present invention. FIG. 3 is a front view schematically showing the automatic blood image analyzer of FIG. 1. FIGS. 3 through 8 illustrate the deployment patterns of the automatic blood image analyzing system of FIG. 1. The structure of an embodiment of the automatic blood image analyzing system of the present invention is described below with reference to FIGS. 1 through 8.

The automatic blood image analyzing system 100 prepares a blood smear (glass slide) in a blood smear preparing device 101, transports the prepared blood sample to a sample image obtaining device 103 by a sample conveying device 102, and obtains and image of the transported blood sample in the sample image obtaining device 103. The obtained image is subjected to digital image processing and the blood cells are automatically classified by a personal computer 104. As shown in FIG. 1, the automatic blood image analyzing system 100 is provided with a blood smear preparing device 101, sample conveying device 102, sample image obtaining device 103, personal computer 104, base unit 105, and base unit 1. The base unit 105 is for the installation of the blood smear preparing device 101. The base unit 1 is for the installation of the sample conveying device 102, sample image obtaining device 103, and personal computer 104. As shown in FIG. 2, the automatic blood image analyzing system 100 of the present embodiment has a variable deployment unit 100a, and a stationary unit 100b. The variable deployment unit 100a has the sample conveying device 102, sample image obtaining device 103, and personal computer 104, and is configured so that the deployment of each device is variable. The stationary unit 100b has the blood smear preparing device 101 and base unit 105, and is positionally fixed relative to a sample conveying line 200. The blood smear preparing device 101, sample conveying device 102, and sample image obtaining device 103 are disposed in a line in a predetermined direction (X direction). The sample conveying line 200, which transports racks 151, is laid out so as to extend in the X direction on the front side of the automatic blood image analyzing system 100. The rack 151 holds test tubes 150 which contain samples (blood) to be analyzed. As shown in FIGS. 1 and 3, the automatic blood image analyzing system 100 is arranged along the sample conveying line 200. A sample conveying line (not shown in the drawings) which extends in the X direction is further connected at both ends of the sample conveying line 200 in the X direction.

The blood smear preparing device 101 takes the sample (blood) from the test tube 150 in the rack 151 which is transported by the sample conveying line 200. The blood smear preparing device 101 prepares a sample for automatic analysis by smearing an obtained sample on a glass slide (not shown in the drawing). This sample is analyzed by the sample image obtaining device 103 and the personal computer 104. A sample acquisition port 101a, which is provided for obtaining the sample (blood) from the test tube 150, is disposed on the front side (the side with the sample conveying line 200) of the blood smear preparing device 101. The sample (glass slide) prepared in the sample smear preparing device 101 is configured to be transferred by the sample conveying device 102.

As shown in FIG. 1, the sample conveying device 102 is provided to transport the sample (glass slide) received from the blood smear preparing device 101 to the sample image obtaining device 103.

The sample image obtaining device 103 has the function of obtaining a blood image of the sample (glass slide) received from the sample conveying device 102, and sending the obtained image data (digital data) to the personal computer 104. The personal computer 104 is connected to the sample image obtaining device 103.

The personal computer (PC) 104 has the functions of performing digital image processing of the sample image (blood image) obtained in the sample image obtaining device 103, and performing automatic classification of the blood cell types, as shown in FIGS. 1 and 2. The personal computer (PC) 104 further has a controller 104a, display 104b, and input unit 104c.

As shown in FIG. 1, the sample conveying line 200 has the function of transporting the rack 151 in the arrow X1 direction along a conveying path 201. Specifically, a rack 151, which has been transported from a connecting part 201a connected to a sample conveying line in the arrow X2 direction (not shown in the drawing), is fed in the arrow Y1 direction in a conveying part 201b. Thereafter, the rack 151 is transported in the arrow Y1 direction to an acquisition position S in front of the sample acquisition port 101a of the blood smear preparation device 101. The sample (blood) held in the test tube 150 at the acquisition position S is taken up by the blood smear preparing device 101 through the sample acquisition port 101a. The rack 150 is then transported from the acquisition position S in the arrow X1 direction. The rack 151 is thereafter transported in the arrow Y2 direction by a conveying unit 201c. The rack 151 is subsequently transported in the arrow X1 direction by a connecting unit 201d. The rack 151 is thus transported to a sample conveying line connected in the arrow X1 direction (not shown in the drawing).

The base unit 105, on which the blood smear preparing device 101 is installed, is stationary relative to the sample conveying line 200. That is, the blood smear preparing device 101 is mounted stationary relative to the sample conveying line 200.

The base unit 1 is configured to have the sample conveying device 102 and sample image obtaining device 103, which are installed on the base unit 1, slidable in the X direction and the Y direction which is perpendicular to the X direction relative to the blood smear preparing device 101. As shown in FIG. 3, the blood smear preparing device 101, sample conveying device 102, and sample image obtaining device 103 are aligned in the X direction when analysis is performed by the automatic blood image analyzing system 1. When performing maintenance or repair work on these devices, the positions of the blood smear preparing device 101, sample conveying device 102, and sample image obtaining device 103 can be changed by sliding the variable deployment unit 100a.

Figure 4:
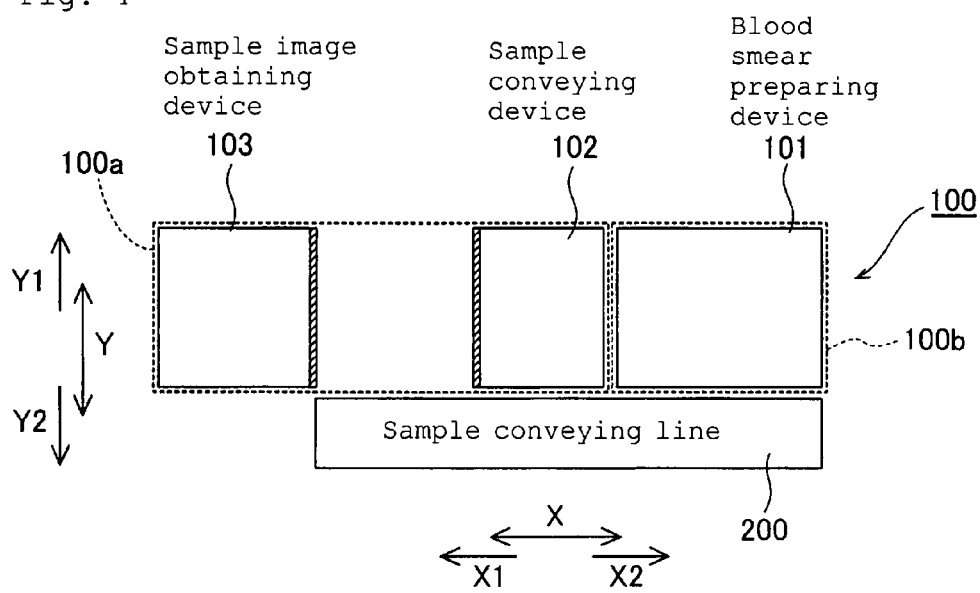
FIG. 4 is a front view schematically showing a sample image obtaining device of the automatic blood image analyzer of FIG. 3 which has been moved in the arrow X1 direction.

Specifically, the deployment positions of the blood smear preparing device 101, sample conveying device 102, and blood image obtaining device 103 can be changed from the positions during analysis as shown in FIG. 3 to the positions shown in FIG. 4. FIG. 4 shows the sample image obtaining device 103 separated from the sample conveying device 102 and by sliding only the sample image obtaining device 103 in the arrow X1 direction. In the deployment positions of FIG. 4, the facing surfaces (the area indicated by the diagonal (hatched) lines in FIG. 4) are exposed between the sample conveying device 102 and sample image obtaining device 103, which confront one another when deployed for analysis (refer to FIG. 3).

Figure 5:
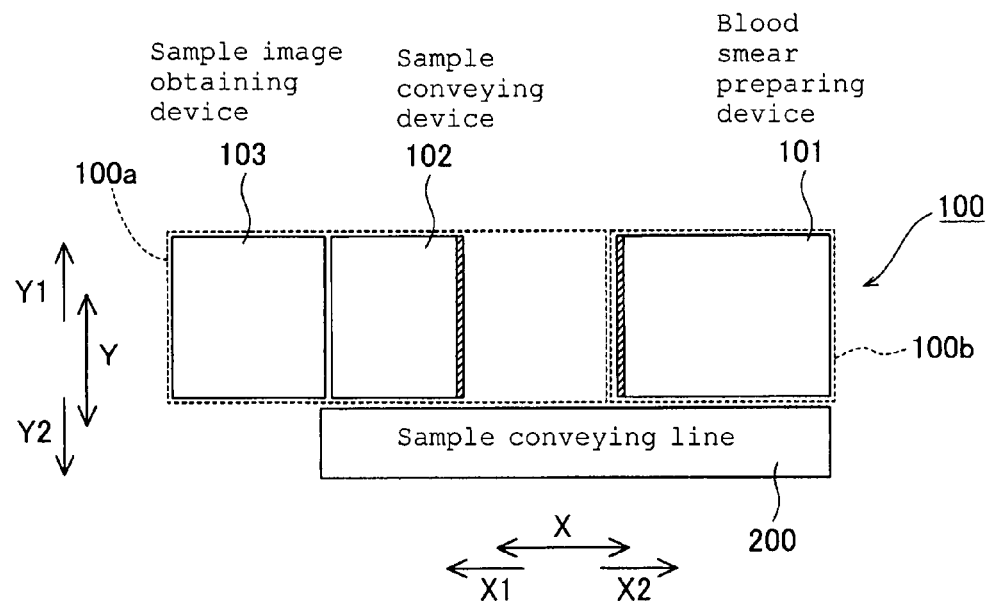
FIG. 5 is a front view schematically showing a sample image obtaining device and sample conveying device of the automatic blood image analyzer of FIG. 3 which have been moved in the arrow X1 direction.

Furthermore, the deployment positions of the blood smear preparing device 101, sample conveying device 102, and blood image obtaining device 103 can be changed from the positions shown in FIG. 3 to the positions shown in FIG. 5. FIG. 5 shows the sample conveying device 102 and the blood smear preparing device 101 in separated deployment positions achieved by sliding the sample conveying device 102 in the arrow X1 direction. In the deployment positions of FIG. 5, the facing surfaces (the area indicated by the diagonal (hatched) lines in FIG. 5) are exposed between the sample conveying device 102 and blood smear preparing device 101, which confront one another when deployed for analysis (refer to FIG. 3).

Figure 6:
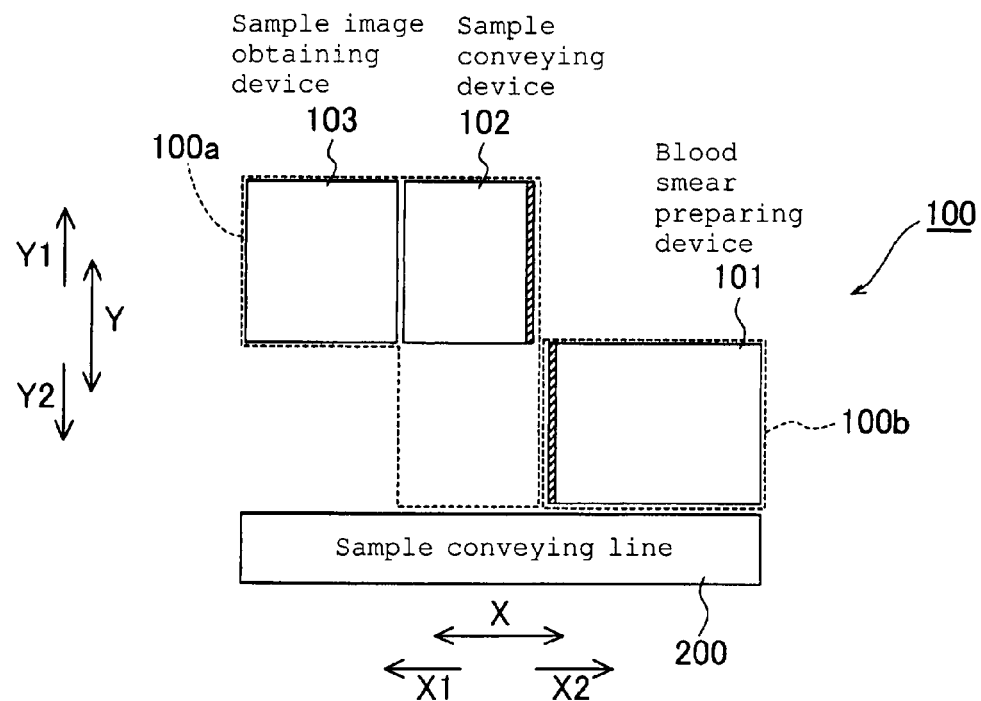
FIG. 6 is a front view schematically showing a sample image obtaining device and sample conveying device of the automatic blood image analyzer of FIG. 3 which have been moved in the arrow Y1 direction.

The deployment of the devices can also be changed from the deployment positions for analysis shown in FIG. 3 to the deployment positions shown in FIG. 6. FIG. 6 shows deployment positions in which the sample conveying device 102 and the sample image obtaining device 103 extend in the arrow Y1 direction relative to the blood smear preparing device 101 by sliding the sample conveying device 102 and sample image obtaining device 103 in the arrow Y1 direction. In the deployment positions of FIG. 6, the facing surfaces (the area indicated by the diagonal (hatched) lines in FIG. 6) are exposed between the sample conveying device 102 and blood smear preparing device 101, which confront one another when deployed for analysis (refer to FIG. 3).

Figure 7:
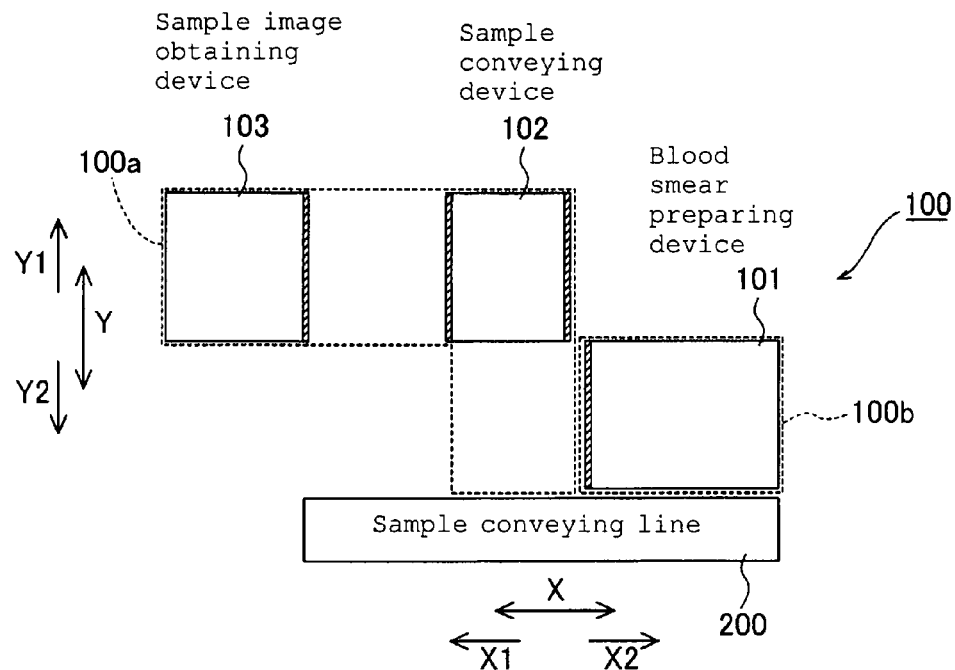
FIG. 7 is a front view schematically showing a sample image obtaining device of the automatic blood image analyzer of FIG. 6 which has been moved in the arrow X1 direction.
Figure 8:
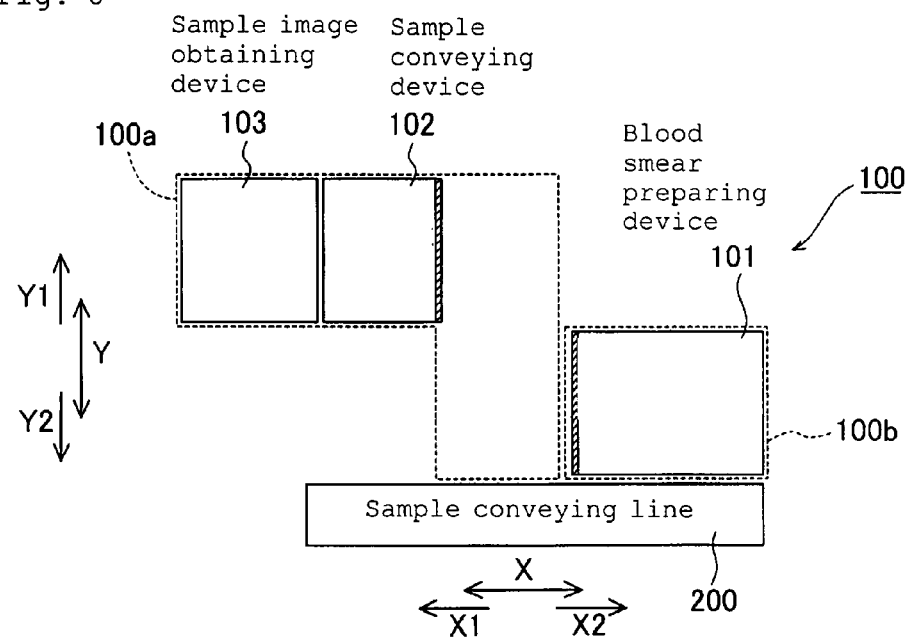
FIG. 8 is a front view schematically showing a sample image obtaining device and sample conveying device of the automatic blood image analyzer of FIG. 6 which have been moved in the arrow X1 direction.

The deployment of the devices can also be changed from the deployment positions shown in FIG. 6 to the deployment positions shown in FIG. 7. In the deployment positions of FIG. 7, the facing surfaces (the area indicated by the diagonal (hatched) lines in FIG. 7) are exposed between the sample conveying device 102 and sample image obtaining device 103, which confront one another when deployed for analysis (refer to FIG. 3) by sliding the sample image obtaining device 103 in the arrow X1 direction. The deployment of the devices can also be changed from the deployment positions for analysis shown in FIG. 7 to the deployment positions shown in FIG. 8. In the deployment positions of FIG. 8, the facing surfaces (the area indicated by the diagonal (hatched) lines in FIG. 8) are exposed between the sample conveying device 102 and blood smear preparing device 101, which confront one another when deployed for analysis (refer to FIG. 3) by sliding the sample conveying device 102 in the arrow X1 direction.

As shown in FIGS. 4 through 8, a user can access each of the devices (blood smear preparing device 101, sample conveying device 102, and sample image obtaining device 103) from the exposed facing surfaces by sliding the variable deployment unit 100a.

Figure 9:
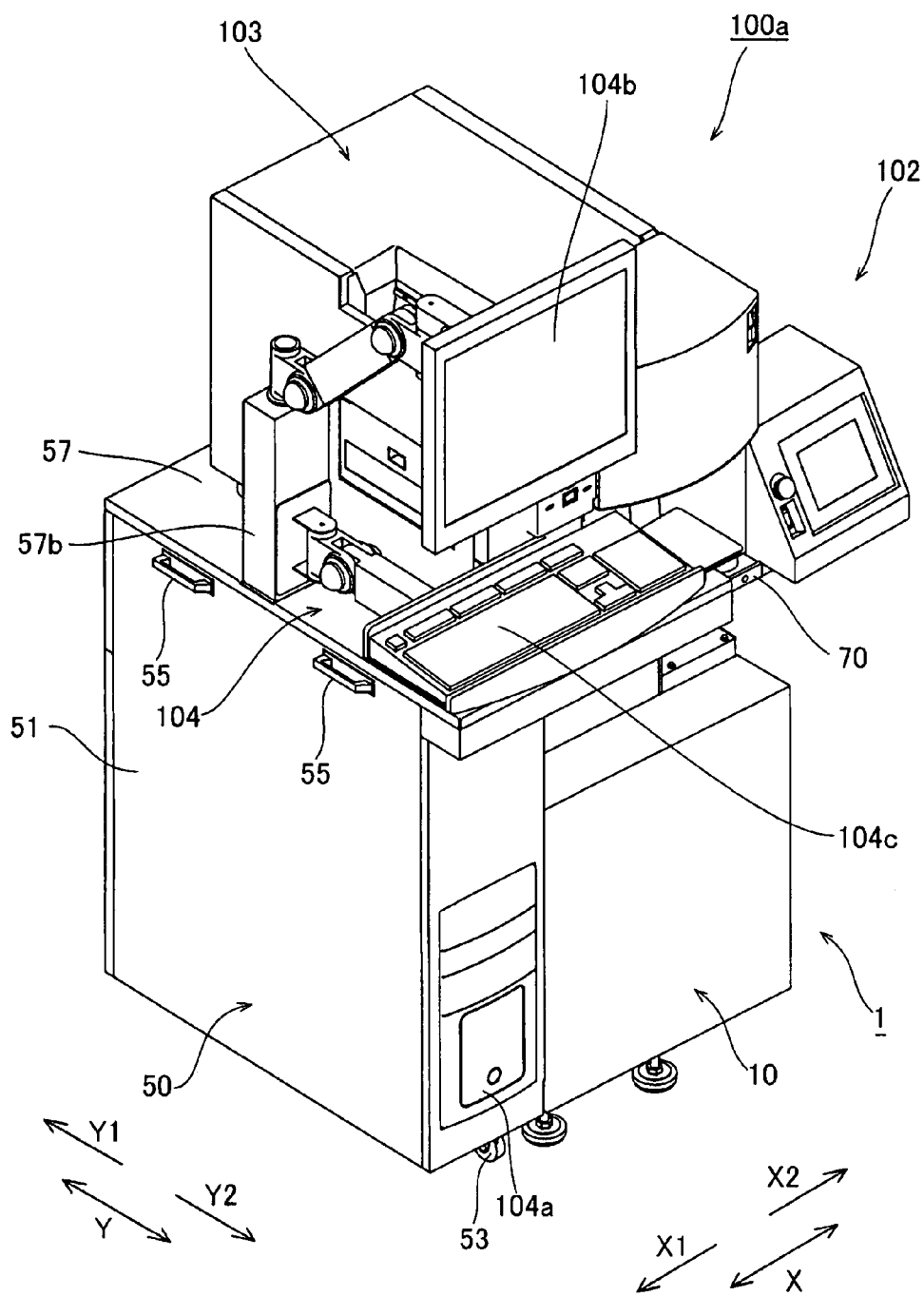
FIG. 9 is a perspective view showing a variable deployment unit of an automatic blood image analyzing system of an embodiment of the present invention.
Figure 10:
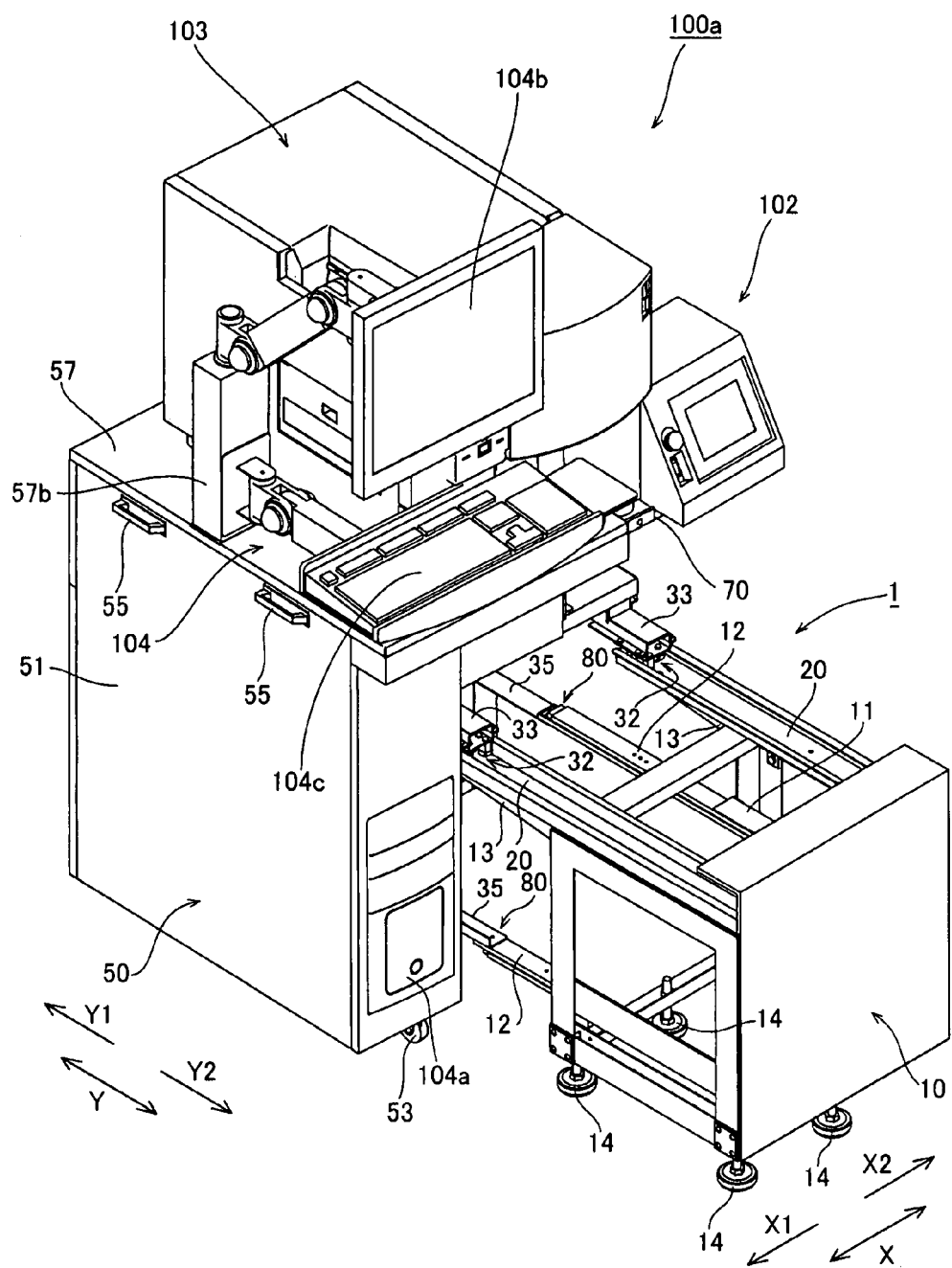
FIG. 10 is a perspective view of the variable deployment unit of FIG. 9 which corresponds to the deployment condition shown in FIG. 6.
Figure 11:
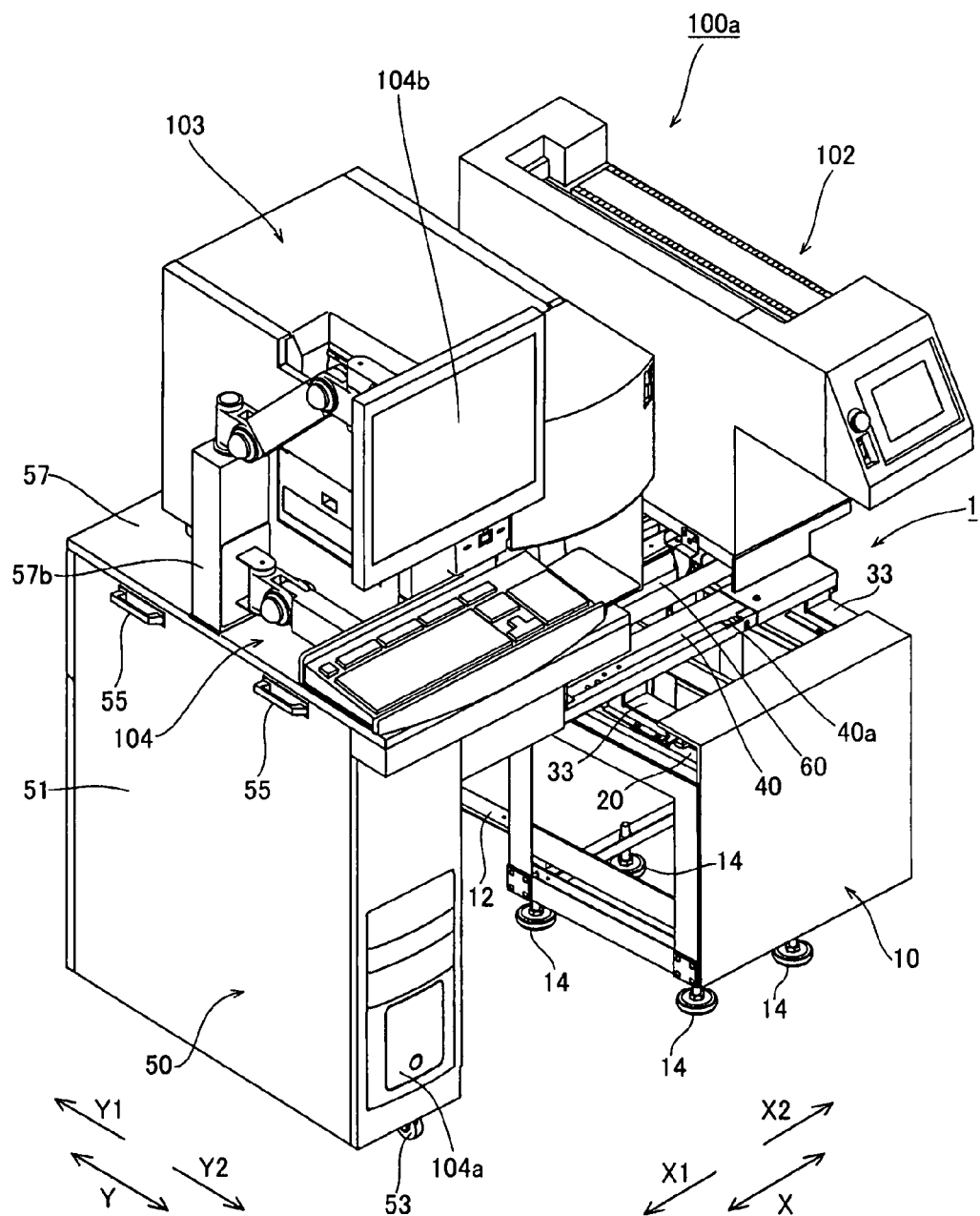
FIG. 11 is a perspective view of the variable deployment unit of FIG. 9 which corresponds to the deployment condition shown in FIG. 5.

FIGS. 9 through 11 are perspective views of the variable deployment unit 100a of the automatic blood image analyzing system of FIG. 1. FIGS. 12 through 22 illustrate structural details of the base unit on which are installed the sample conveying device and sample image obtaining device of the variable deployment unit shown in FIGS. 9 through 11. Structural details of the base unit 1 on which are installed the sample conveying device 102 and sample image obtaining unit 103 are described below with reference to FIG. 2 and FIGS. 9 through 22.

As shown in FIG. 2 and FIGS. 9 through 14, the base unit 1 includes a stationary part 10, two slide rails 20, a moving part 30 (refer to FIG. 13), two slide rails 40, a moving part 50, two slide rails 60, and a moving part 70. The stationary part 10 is fixedly installed so that the blood smear preparing device 101 is adjacent to the side of the base unit 105 in the arrow X1 direction (refer to FIG. 2). The two slide rails 20 are fixedly attached to the stationary part 10 and extend in the Y direction. The moving part 30 is movable in the Y direction along the slide rails 20. The two slide rails 40 are fixedly attached to the moving part 30 and extend in the X direction. The moving part 50 has the sample image obtaining device 103 installed thereon and is movable in the X direction along the slide rails 40. The two slide rails 60 are fixedly attached to the moving part 30 and extend in the X direction. The moving part 70 has the sample conveying device 102 installed thereon and is movable in the X direction along the slide rails 60.

Figure 13:
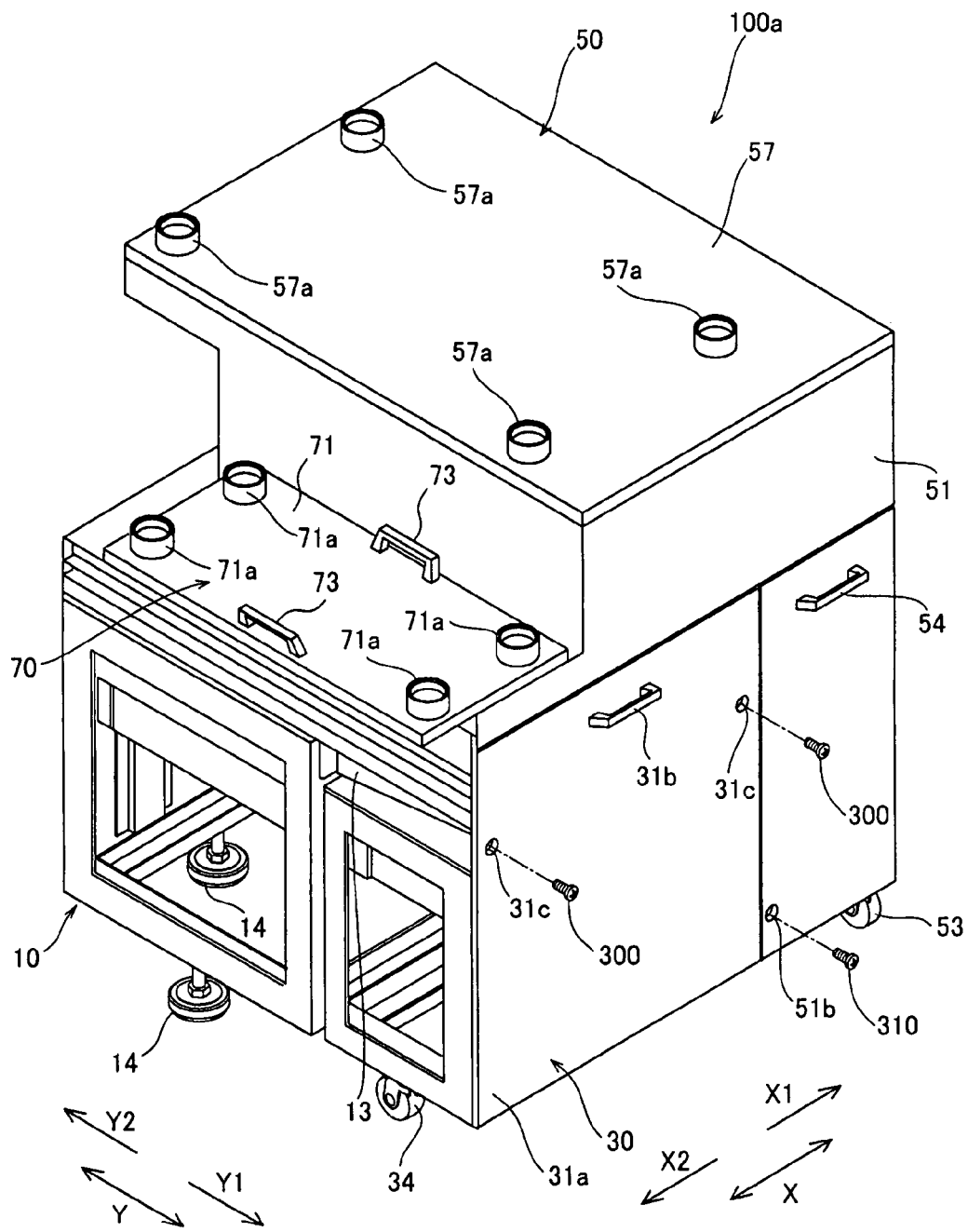
FIG. 13 is a perspective view showing the base unit of FIG. 12 when viewed from behind.
Figure 16:
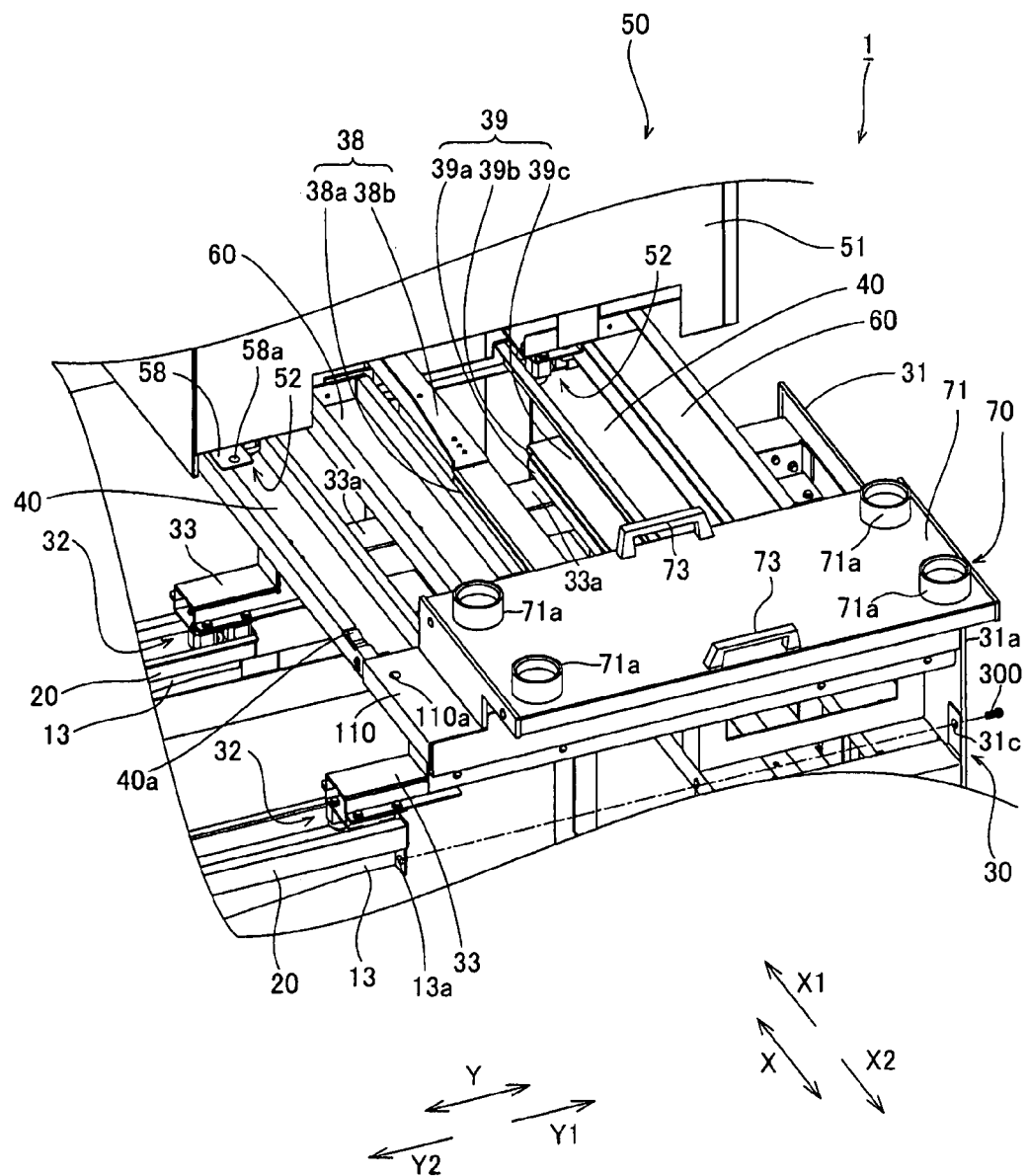
FIG. 16 is an enlarged perspective view of the base unit of FIG. 14 when viewed from another direction.

As shown in FIG. 10, two guide base ends 11, which project to extend in the arrow Y1 direction toward the moving part 30, are fixedly attached to the stationary part 10. Slide members 12 are mounted on the guide base ends 11, and are slidable in the Y direction relative to the guide base ends 11. As shown in FIGS. 13 and 16, two projections 13 are provided on the stationary part 10 so as to project in the arrow Y1 direction toward the moving part 30 below the respective slide rails 20. The leading ends of the two projections 13 on the moving part 30 side are provided with a screw holes 13 (refer to FIG. 16) into which a screw 300 (refer to FIGS. 13 and 16) is inserted to secure the stationary part 10 and moving part 30. A plurality of support legs 14 are provided on the bottom surface of the stationary part 10 to prevent the stationary part 10 from moving.

Figure 15:
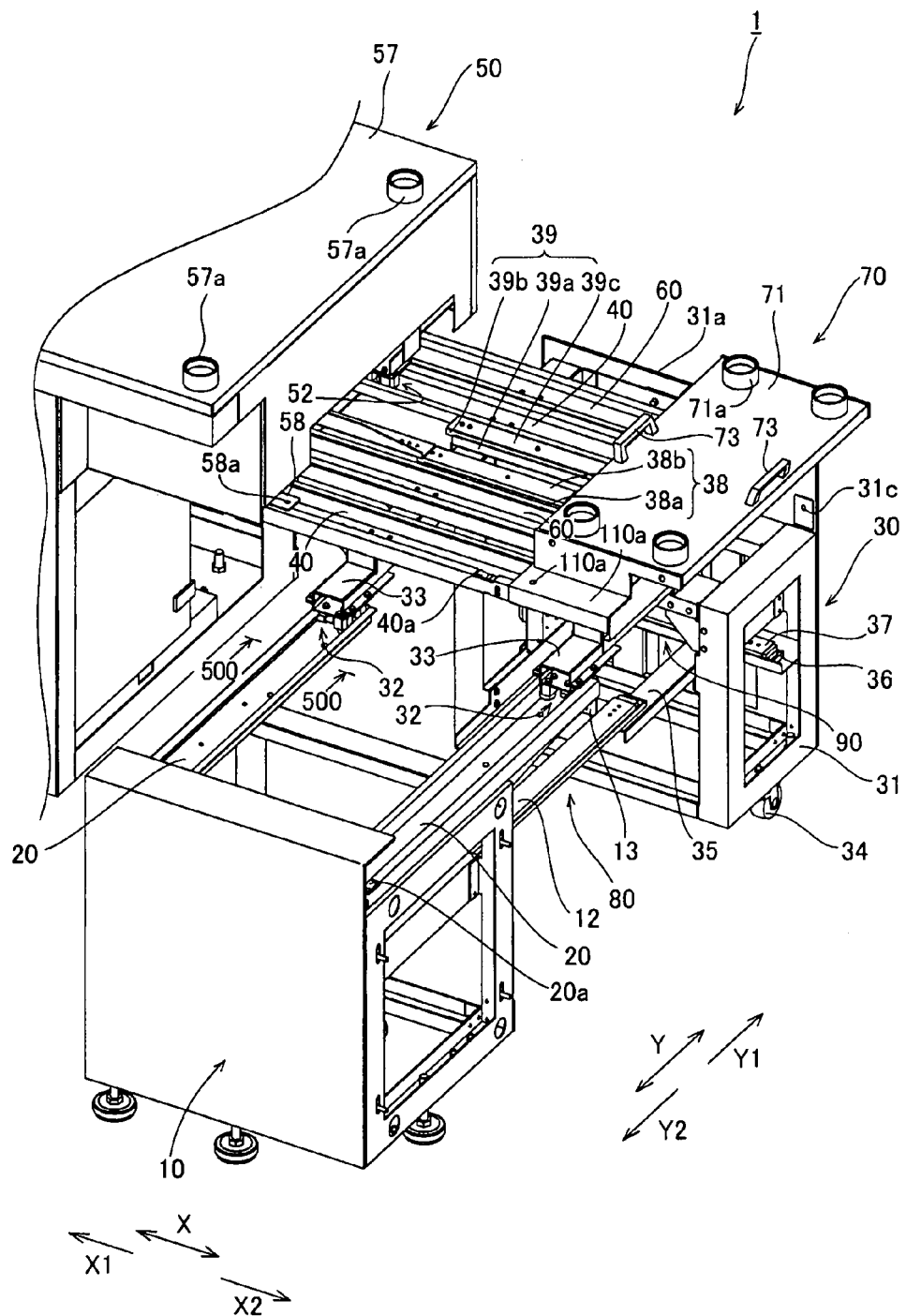
FIG. 15 is a perspective view of the base unit of FIG. 14 when viewed from another direction.

As shown in FIG. 15, the slide rails 20 are fixedly attached to the top surface of the stationary part 10. Furthermore, an elastically deformable flat spring type stopper 20a is provided at the end of the rail 20 on side in the arrow Y2 direction. The stopper 20a prevents the moving part 30 from moving relative to the stationary part 10 when the stationary part 10 and the moving part 30 are in a closed condition.

As shown in FIGS. 15 and 16, the moving part 30 has a moving body 31, oscillating part 32, two slide rail support members 33, and a plurality of casters 34. The two oscillating parts 32 are movable in the Y direction along the two slide rails 20. The two slide rail support members 33 are fixedly attached to the moving body 31 and the two oscillating parts 32. Furthermore, the slide rails 40 and 60 are fixedly attached to the two slide rail support members 33. The plurality of casters 34 are mounted on the bottom surface of the moving body 31 to support the moving body 31 so as to be movable. Therefore, the moving body 31, with the casters 34 mounted on the bottom surface thereof, is fixedly attached through the slide rail support members 33 to the oscillating part 32, which is movable in the Y direction. The moving part 30 is thus configured to be slidable in the Y direction relative to the stationary part 10.

Figure 14:
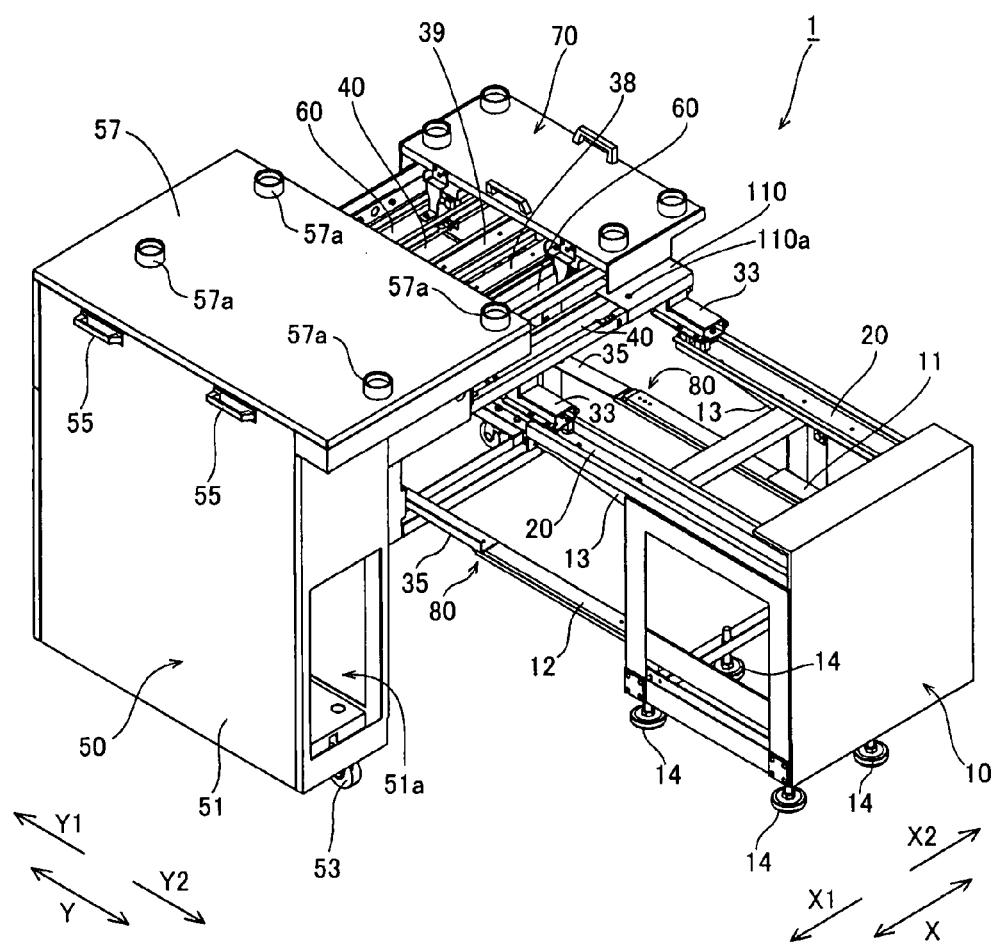
FIG. 14 is a perspective view of the base unit of FIG. 12 which corresponds to the deployment condition shown in FIG. 7.

As shown in FIGS. 14 and 15, two slide connectors 35 are fixedly attached to the moving body 31 and project so as to extend in the arrow Y2 direction toward the stationary part 10 side. The slide connector 35 is provided at a position which corresponds to the previously mentioned slide member 12 and guide base end 11 of the stationary part 10. The slide connector 35 is fixedly attached to the slide member 12 mounted on the guide base end 11 of the stationary part 10. The sliding movement of the moving part 30 is guided in the Y direction relative to the stationary part 10 by a slide guide 80 which is configured buy the slid connector 35, guide base end 11, and slide member 12.

Figure 22:
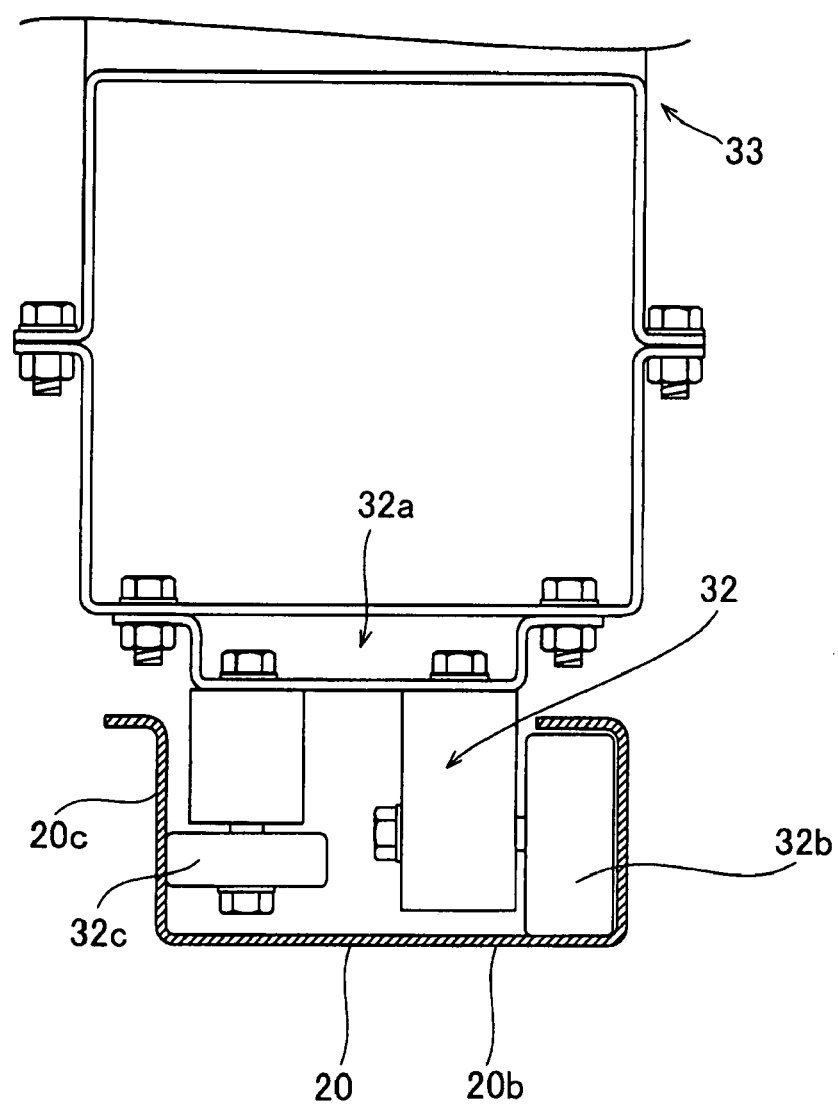
FIG. 22 is a cross section view of the slide rail and oscillating part along the 500-500 line of FIG. 15.

The oscillating part 32 has the structure shown in FIG. 22. A metal roller 32b and a rubber roller 32c are mounted on an oscillating body 32a which is mounted on the slide rail support member 33. The roller 32b rotates on the bottom surface 20b of the slide rail 20. The roller 32b supports the load above. The roller 32c rotates along the side surface 20c of the slide rail 20. The roller 32c smoothly oscillates the oscillating part 32. The metal roller 32b is latched and held by the flat spring stopper 20a (refer to FIG. 15) of the slide rail 20. Thus, the moving part 30 is prevented from moving relative to the stationary part 10 when the stationary part 10 and the moving part 30 are closed.

As shown in FIG. 15, one guide base end 36 is fixedly attached to the moving body 31 so as to extend in the arrow X1 direction toward the moving part 60 side. A slide member 37 is mounted on the guide base end 36, and is slidable in the X direction relative to the guide base end 36. As shown in FIG. 13, a handle 31b and two screw holes 31c are provided on the wall 31a on the back side of the moving body 31. The handle 31b is provided for a user can grasp when moving the moving part 30 and the moving part 60 in the Y direction. Screws 300 are inserted into the screw holes 31c to fixedly attach the stationary part 10 and the moving part 30. When the stationary part 10 and the moving part 30 are in a closed condition, the two screw holes 31c of the moving part 30 and the screw holes 13a (refer to FIG. 16) respectively provided on the two projections 13 of the stationary part 10 are engaged by the screws 300. Therefore, the stationary part 10 and the moving part 30 are configured so as to be fixedly attached together. Furthermore, a screw hole (not shown in the drawings) is provided on the back part of the moving body 31 (refer to FIG. 15) at a position corresponding to the screw hole 51b (refer to FIG. 13) of a moving part 50 which is described later, and a screw 310 (refer to FIG. 13 is inserted into this screw hole to fixedly attach the moving part 30 and the moving part 70.

Figure 18:
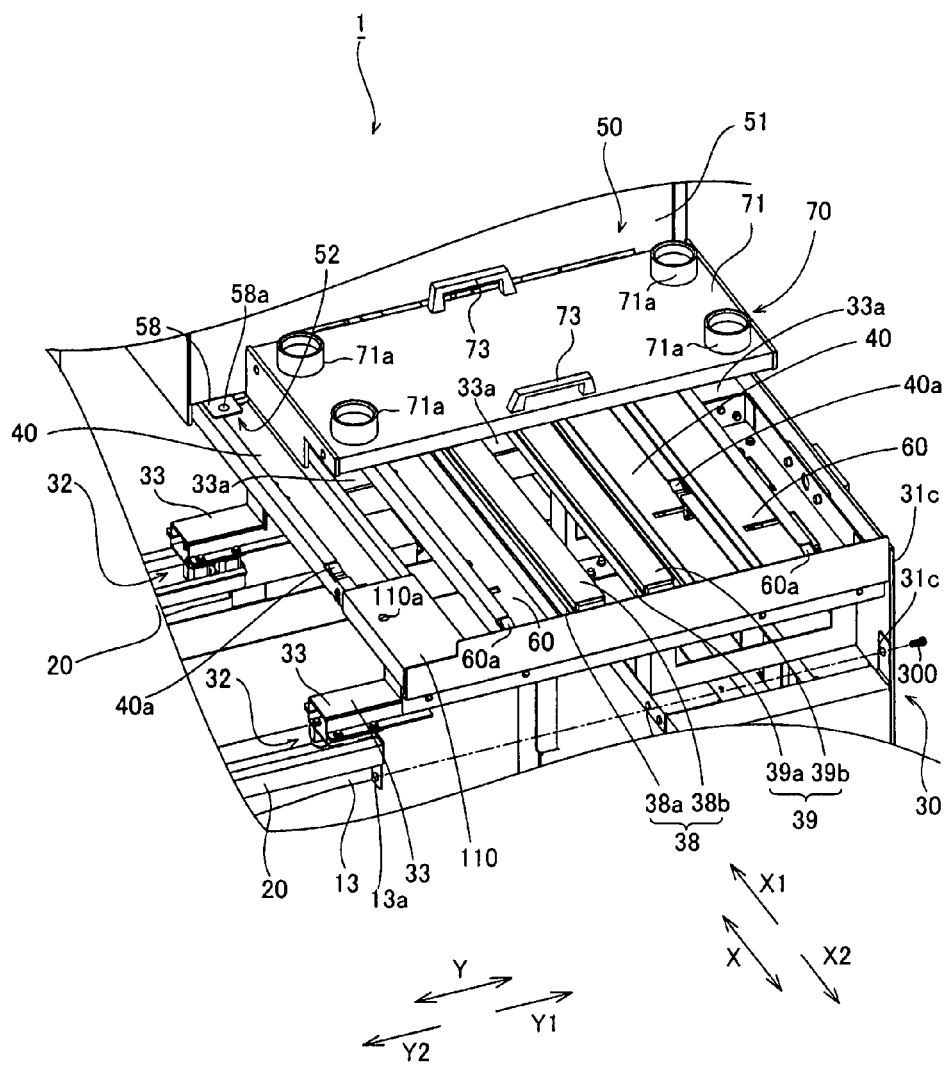
FIG. 18 is an enlarged perspective view of the base unit of FIG. 16 which corresponds to the deployment condition shown in FIG. 8.
Figure 20:
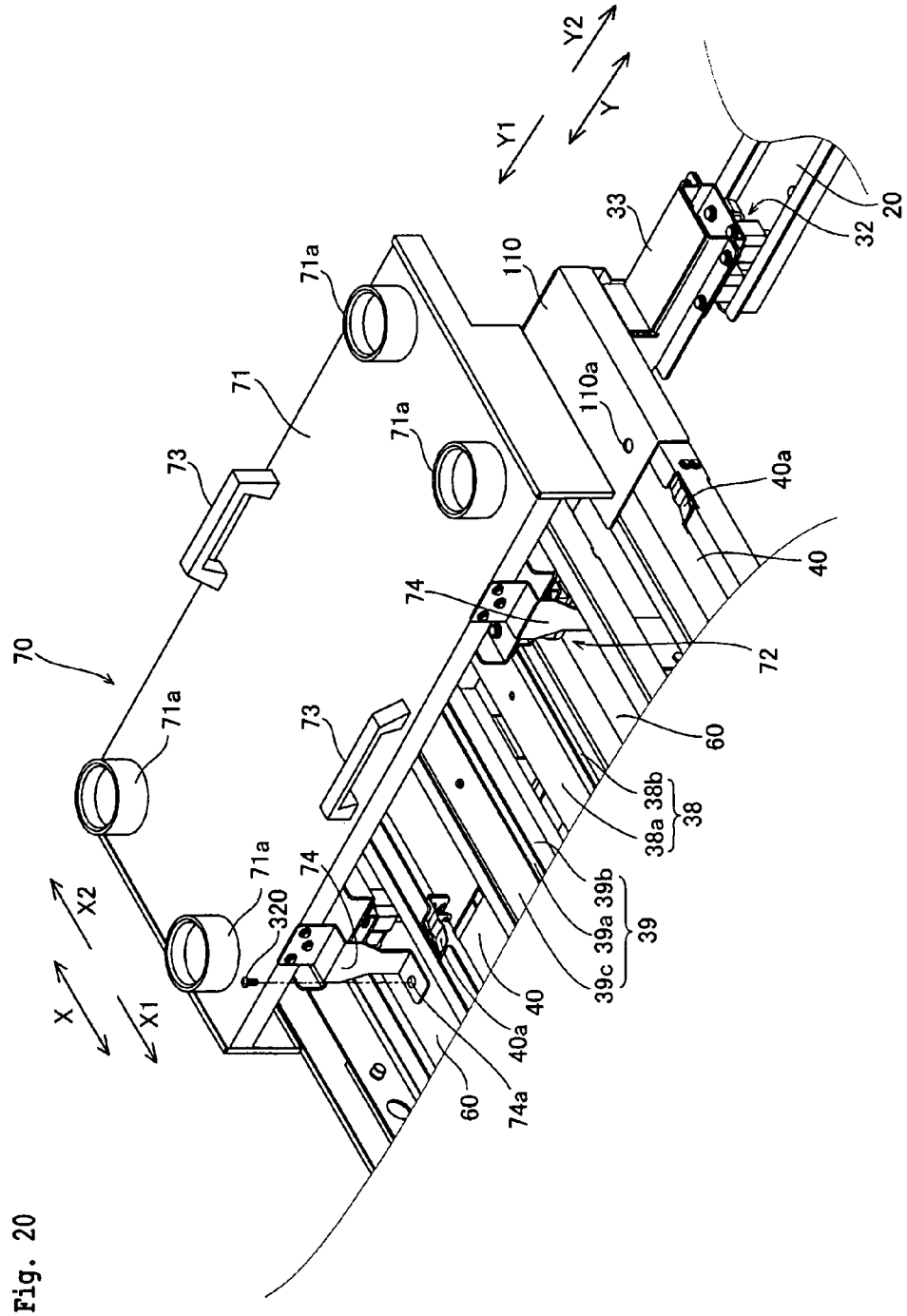
FIG. 20 is an enlarged perspective view of the base unit of FIG. 14.
Figure 21:
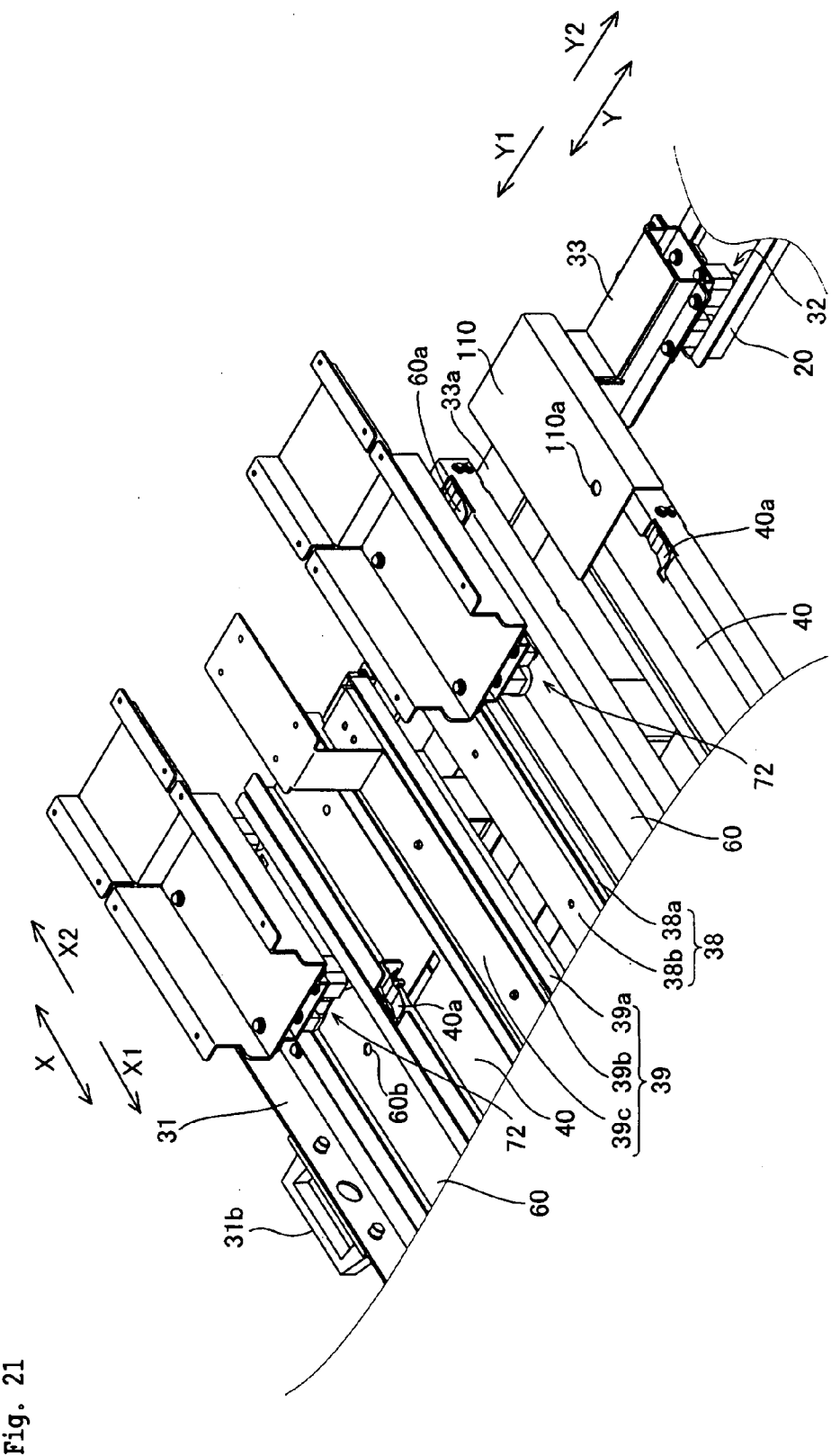
FIG. 21 is an enlarged perspective view showing the installation unit and various covers removed from the mounting base of FIG. 14.

As shown in FIGS. 16 and 18, fixedly attached to the top surface 33a of the slide rail support member 33 are a direct-acting guide 38 for guiding the movement of the moving part 50 in the X direction, and a direct-acting guide 39 for guiding the movement of the moving part 70 in the X direction. The direct-acting guide 38 has a slide rail 38a and a slider 38b. Slide rail 38a is fixedly attached to the top surface 33a of the slide rail support member 33. The slider 38b is mounted so as to be slidable in the X direction on the slide rail 38a. The slider 38b is fixedly attached to the moving part 50. The direct-acting guide 39 has a slide rail 39a, a slider 39b, and a mounting member 39c (refer to FIG. 21). The slide rail 39a is fixedly attached to the slide rail support member 33. The slider 39b is mounted so as to be slidable in the X direction on the slide rail 39a. The mounting member 39c is mounted on the top surface of the slider 39b, and is fixedly attached to the moving part 70. As shown in FIGS. 20 and 21, a plate member 110 is fixedly attached to the top surface 33a of the slide rail support member 33. A screw hole 110a is provided in the plate member 110, and a screw 311 is inserted into this screw hole to fixedly attach the moving part 50 to the moving part 30.

The slide rail 40 is fixedly attached to the top surfaces 33a of the two slide rail support members 33 of the moving part 30. As shown in FIG. 21, an elastically deformable flat spring stopper 40a is provided at a position a predetermined distance from the end part of the slide rail 40 in the arrow X2 direction. The stopper 40a prevents the moving part 50 from moving once the moving part 50 has been moved in the arrow X2 direction. Since the specific structure of the slide rail 40 and an oscillating part 52 of the moving part 50, which is described later, are respectively identical to structure of the previously mentioned slide rail 20 and the oscillating part 32 of the moving part 30 (refer to FIG. 22), detailed description is omitted.

Figure 12:
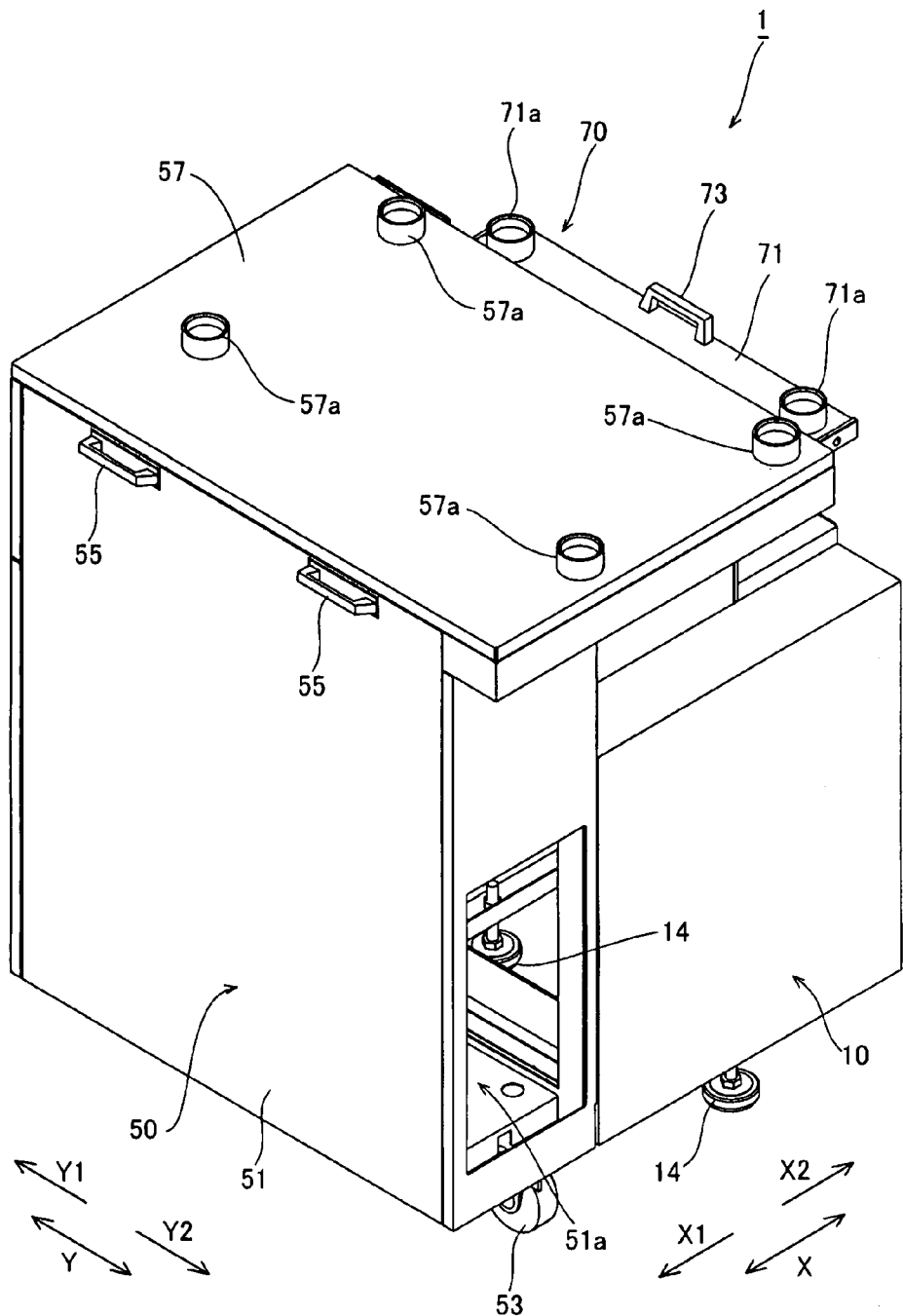
FIG. 12 is a perspective view showing a base unit of an automatic blood image analyzing system of an embodiment of the present invention.
Figure 19:
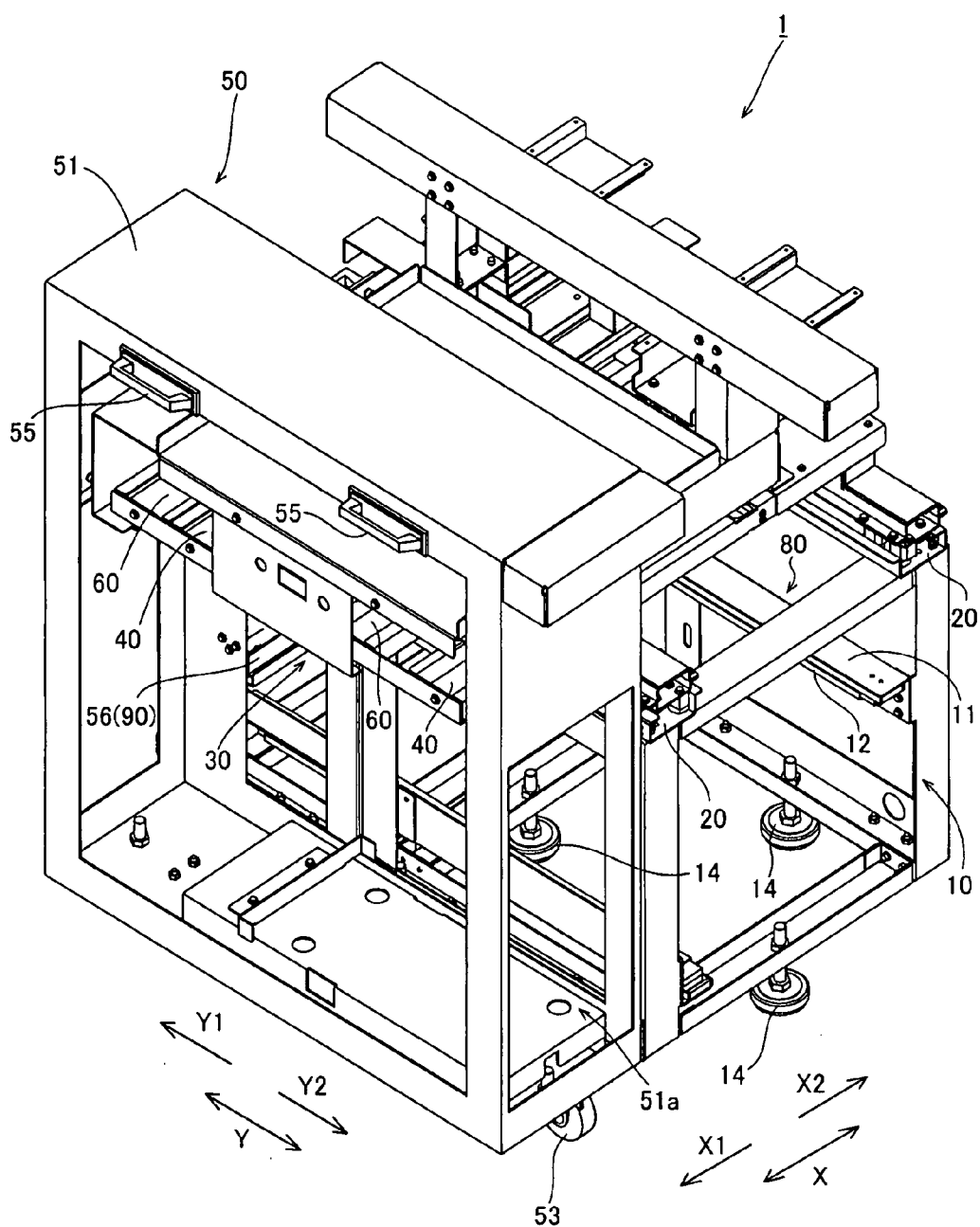
FIG. 19 is a perspective view showing the installation unit and various covers removed from the mounting base of FIG. 12.

As shown in FIGS. 12 through 16, the moving part 50 has a moving body 51, two oscillating parts 52, a plurality of casters 53, a handle 54 (refer to FIG. 13), and two handles 55 (refer to FIG. 12). The plurality of casters 53 are mounted on the bottom surface of the moving body 51 to support the moving body 51 so as to be movable. The handle 54 is provided for the user to grasp when moving the moving part 30 and the moving part 50 in the Y direction relative to the stationary part 10. The two handles 55 are provided for the user to grasp when moving the moving part 50 in the X direction relative to the stationary part 10. As shown in FIG. 19, one slide connector 56 is fixedly attached to the moving body 51 so as to extend in the arrow X2 direction toward the moving part 30 side. The slide connector 56 is provided at a position corresponding to the guide base end 35 (refer to FIG. 15) and the slide member 37 (refer to FIG. 15) of the previously mentioned moving part 30. The slide connector 56 is fixedly attached to the slide member 37 mounted on the guide base end 36 of the moving part 30. The movement of the moving part 50 relative to the moving part 30 is guided in the X direction by the direct-acting guide 38 and a slide guide 90 which is configured by the slide connector 56, the guide base end 36, and the slide member 37.

Figure 17:
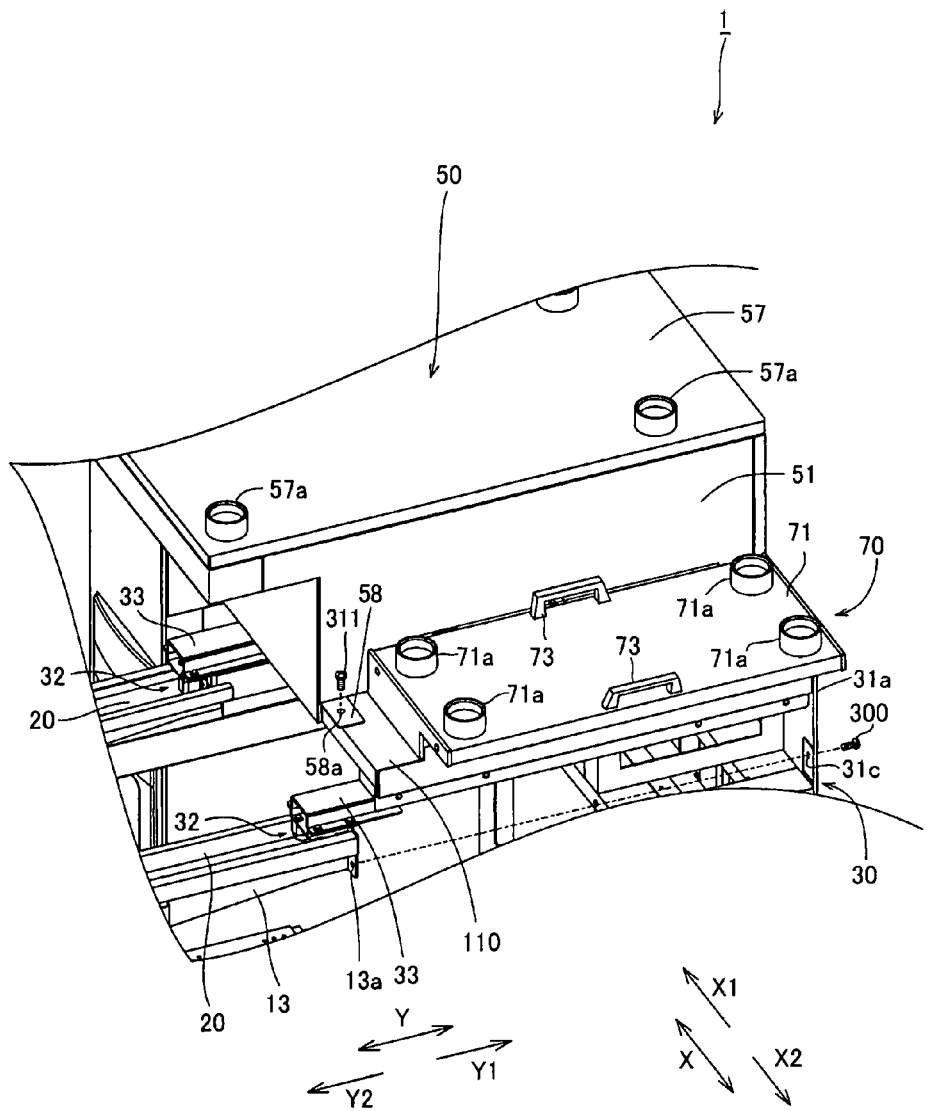
FIG. 17 is an enlarged perspective view of the base unit of FIG. 16 which corresponds to the deployment condition shown in FIG. 6.

As shown in FIGS. 9 through 12, the controller 104a of the personal computer 104 is housed in the control housing 51a of the moving body 51 (refer to FIG. 12). An mounting base 57 is provided on the top surface of the moving body 51 for installing the sample image obtaining device 103. The sample image obtaining device 103 is installed on the mounting base 57 positioned on four cylindrical convex parts 57a provided on the mounting base 57. A support arm 57b for mounting the display 104b and input part 104c of the personal computer 104 is fixedly attached to the mounting base 57. As shown in FIGS. 16 and 17, a protruding tab 58 is mounted on the side surface of the moving body 51 on the moving part 70 side. A screw hole 58a is provided in the protruding tab 58 through which is inserted a screw 311 (refer to FIG. 17) for fixedly attaching the moving part 50. As shown in FIG. 13, the back part of the moving body 51 is provided with a screw hole 51b at a position corresponding to a screw hole (not shown in the drawing) provided on the back part of the previously mentioned moving part 30, and through the screw hole 51b is inserted a screw 310 for fixedly attaching the moving part 70 and the moving part 30. When the moving part 70 and the moving part 50 have been moved in the arrow X2 direction as shown in FIG. 17, the screw 311 engages the screw hole 58a provided in the protruding tab 58 of the moving part 50 and the screw hole 110a provided in the plate member 110 which is fixedly attached to the slide rail support member 33 of the moving part 30. Thus, the configuration fixedly attaches the moving part 50 to the moving part 30. In this condition, the screw 310 engages the screw hole (not shown in the drawing) provided on the back part of the moving part 30 and the screw hole 51b of the moving part 50. Therefore, the moving part 50 and the moving part 30 are configured so as to be fixedly attached together.

The two slide rails 60 are fixedly attached to the top surface 33a of the two slide rail support members 33 of the moving part 30. As shown in FIGS. 18 and 21, an elastically deformable flat spring stopper 60a is provided on the end of the slide rail 60 on the side in arrow X2 direction. The stopper 60a prevents the moving part 70 from moving relative to the moving part 30 once the moving part 70 has been moved in the arrow X2 direction. A screw hole 60b (refer to FIG. 21) is provided on the bottom surface of the respective two slide rails 60. A screw 320 (refer to FIG. 20) is inserted into the screw hole 60b to fix the position of the moving part 70 when the moving part 70 has been moved in the X2 direction. Since the specific structure of the oscillating part 72 of the moving part 70, which is described later, and the structure other than that of the slide rail 60 are respectively identical to structure of the previously mentioned slide rail 20 and the oscillating part 32 of the moving part 30, detailed description is omitted.

The moving part 70 has a mounting base 71 for installing the sample conveying device 102, two oscillating parts 72 fixedly attached to the mounting part 71, and two handles 73 for a user to grasp to move the moving part 70 in the X direction relative to the moving part 30, as shown in FIG. 20. The sample conveying device 102 is installed on the mounting base 71 so as to be positioned on four cylindrical convex parts 71a provided on the mounting base 71. The slider 39a of the direct-acting guide 39 is fixedly attached to the mounting base 71 through the mounting member 39c. Thus, the movement of the mounting base 71 is guided along the X direction. Furthermore, a fixing tab 74 is attached to the mounting base 71. The fixing tab 74 has a screw hole 74a into which a screw 320 is inserted to fix the position of the moving part 70. When the moving part 70 has been moved in the arrow X2 direction, the screw 320 (refer to FIG. 20) engages the screw hole 60b (refer to FIG. 21) provided in the respective slide rails 60, and the screw hole 74a (refer to FIG. 20) of the fixing tab 74 which is attached to the moving part 70. Thus, the configuration fixedly attaches the moving part 70 to the slide rail 60.

In the present embodiment, the sample conveying device 102 and the sample image obtaining device 103 are slidable in the X direction by the base unit 1 on which are installed the sample conveying device 102 and the sample image obtaining device 103 as described above. Furthermore, the sample conveying device 102 and the sample image obtaining device 103 are slidable in the Y direction by the base unit 1. Therefore, the sample conveying device 102 and the sample image obtaining device 103 installed on the base unit 1 are movable not only in the X direction, but also the Y direction relative to the blood smear preparing device 101. For example, in this way the facing surfaces of the blood smear preparing device 101 and the sample conveying device 102, and the facing surfaces of the sample conveying device 102 and the sample image obtaining device 103 can be opened by moving the sample conveying device 102 and the sample image obtaining device 103 in the Y direction even when the automatic blood image analyzing system 100 has been installed at a location in which there is an obstruction on the X direction side of the sample conveying device 102 and the sample image obtaining device 103. Maintenance and repair of the blood smear preparing device 101, sample conveying device 102, and sample image obtaining device 103 can therefore be easily performed through the opened facing surfaces. Accordingly, limitations are therefore eased on the installation location due to obstructions in the automatic blood analyzing system 100 of the present embodiment. Maintenance and repair of the devices (blood smear preparing device 101, sample conveying device 102, and sample image obtaining device 103) are also easily performed.

In the present embodiment, the slide rails 40 and 60 are fixedly attached to the moving part 30, which is movable in the Y direction relative to the stationary part 10 as described above. Furthermore, the sample image obtaining device 103 is installed on the moving part 50, which is movable in the X direction along the slide rail 40. Moreover, the sample conveying device 102 is installed on the moving part 70, which is movable in the X direction along the slide rail 60. In this way the sample conveying device 102 and the sample image obtaining device 103 can be slidably moved in the X direction, and the ample conveying device 102 and the sample image obtaining device 103 can be slidably moved in the Y direction.

In the present embodiment, the guide base end 36 and slide member 37 of the moving part 30, and the slide connector 56 of the moving part 50 are connected. Further, the moving part 50 is mounted on the slider 38b of the direct-acting guide 38, which is fixedly attached to the moving part 30. The moving part 50 on which is installed the sample image obtaining device 103 can therefore be guided so as to move in the X direction by the slide guide 90 and the direct-acting guide 38. Furthermore, the movement of the moving part 50 is performed smoothly in the X direction relative to the moving part 30. The movement of the moving part 70, on which the sample conveying device 102 is installed, relative to the moving part 30 can be guided in the X direction by mounting the moving part 70 on the slider 39b of the direct-acting guide 39 which is attached to the moving part 30. Thus, the movement of the moving part 70 is performed smoothly in the X direction relative to the moving part 30.

The present embodiment has the slide guide 80 which is configured by the guide base end 11 and slide member 12 of the stationary part 10, and the slide connector 35 of the moving part 30. The movement of the moving part 30 is therefore guided in the Y direction relative to the stationary part 10. Thus, the movement of the moving part 30 is performed smoothly in the Y direction relative to the stationary part 10.

In the present embodiment, the stationary part 10 and moving part 30, the moving part 30 and moving part 50, the moving part 70 and slide rail 60 are respectively attached by screws 300, 310, 311, and 320. The blood smear preparing device 101, sample conveying device 102, and sample image obtaining device 103 can therefore be fixed in a deployment condition arrayed in the X direction during the sample (blood) processing operation by the automatic blood image analyzing system 100.

In the present embodiment, the moving part 30 of the base unit 1 is provided with a handle 31*b*, the moving part 50 is provided with handles 54 and 55, and the moving part 70 is provided with a handle 73. In this way a user can grasp the handles 31*b*, 54, 55, and 73. The sample conveying device 102 and the sample image obtaining device 103 can therefore be easily moved relative to the blood smear preparing device 101.

In the automatic blood image analyzing system 100 the present embodiment, the sample conveying device 102 and the sample image obtaining device 103 are movable in the X and Y directions relative to the blood smear preparing device 101 even when the blood smear preparing device 101, sample conveying device 102, and sample image obtaining device 103 are deployed along the sample conveying line 200. Maintenance and repair operations can therefore be performed on the blood smear preparing device 101, sample conveying device 102, and sample image obtaining device 103.

The embodiment of the present disclosure is in all aspects an example and should be considered in any way limiting. The scope of the present invention is defined by the scope of the claims and not be the description of the embodiment, and includes all modifications within the scope of the claims and the meanings and equivalences therein.

For example, although an example of the present invention applied to an automatic blood analyzing system 100 for imaging and analyzing the image of a sample (blood) has been described in the embodiment above, the present invention is not limited to this embodiment. The present invention may also be applied to other analyzing systems which use different analyzing objects and analyzing methods and the like.

Furthermore, the base unit 105 on which is installed the blood smear preparing device 101, and the base unit 1 on which are installed the sample conveying device 102 and the sample image obtaining device 103 are separate in the example described in the embodiment above. However, the present invention is not limited to this configuration inasmuch as the base unit 105 and the base unit 1 may be integrated as a single unit.

Figure 23:
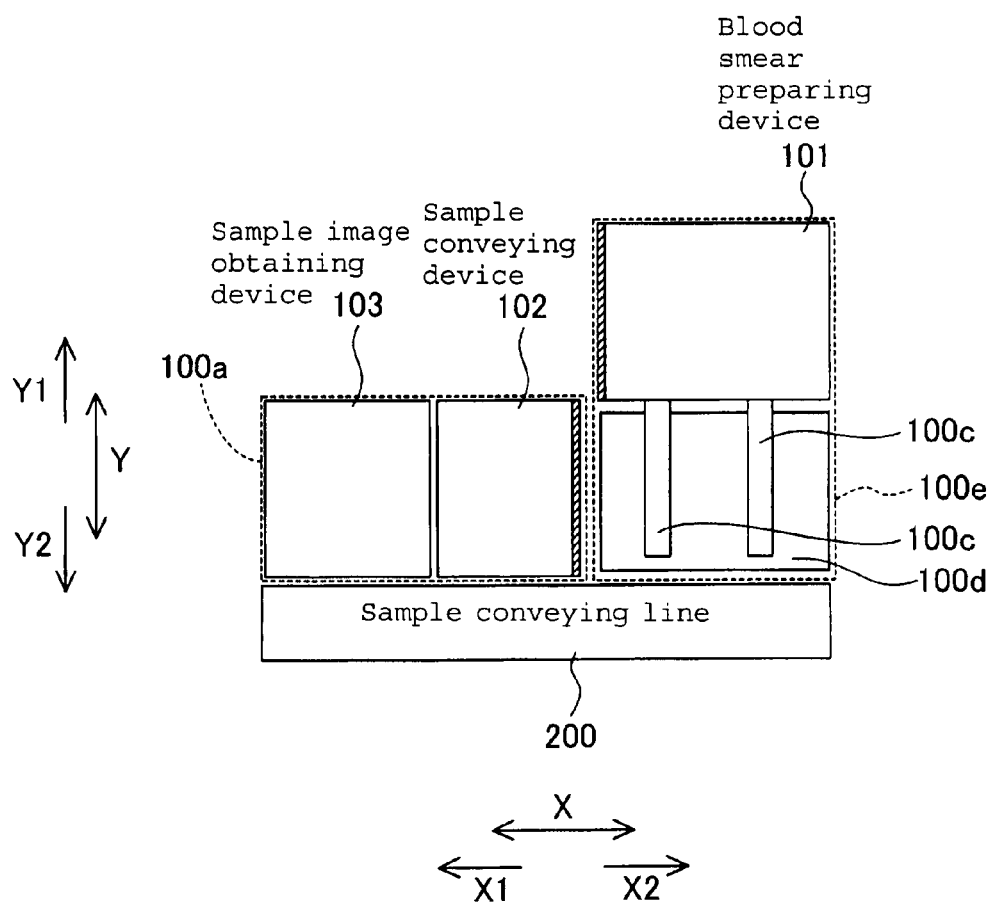
FIG. 23 is a front view schematically showing the blood smear preparation device of the automatic blood image analyzing system of a modification of the embodiment of the present invention when the blood smear preparation device has been moved in the arrow Y1 direction.

The blood smear preparing device 101 is fixedly deployed relative to the sample conveying line 200 in the example described in the embodiment above. However, the present invention is not limited to this configuration. A variable deployment unit 100*e*, on which the blood smear preparing device 101 is installed, may also be provided on a base unit 100*d* which has a slide mechanism 100*c* that is slidable in the Y direction, as in the modification shown in FIG. 23. In this way the blood smear preparing device 101 is also slidable in the Y direction relative to the sample conveying device 102 and the sample image obtaining device 103. As shown in FIG. 23, maintenance and repair operations can be performed on the blood smear preparing device 101 and the sample conveying device 102 from the opened facing surfaces (the areas indicated by the diagonal lines in FIG. 23) by moving only the blood smear preparing device 101 in the Y direction.

The stationary part 10, moving part 30, moving part 50, and moving part 70 are described in the example of the embodiment above as only being fixed when the stationary part 10 and the moving part 30 are in the closed condition, or when the moving part 30, moving part 50, and moving part 70 are in the closed condition. However, the present embodiment is not limited to this configuration inasmuch as the stationary part 10 and the moving part 30 may also be fixed in the open condition for maintenance and repair, and the moving part 30, moving part 50, and moving part 70 may also be fixed in the opened condition. Maintenance and repair can therefore be easily performed.

The present embodiment has been described by way of an example in which both the sample conveying device 102 and the sample image obtaining device 103 can be simultaneously moved in the Y direction relative to the blood smear preparing device 101. However, the present invention is not limited to this configuration. The sample conveying device 102 and the sample image obtaining device 103 may also be moved independently in the Y direction relative to the blood smear preparing device 101. In this case, for example, a guide rail used by the moving part 50 for moving the moving part 50 in the Y direction, and a guide rail used by the moving part 70 for moving the moving part 70 in the Y direction may be provided, and the guide rail of the moving part 50 can be movably guided by the guide rail 40, and the guide rail used by the moving part 70 can be movably guided by the guide rail 60.

What is claimed is:

1. A sample processing system comprising:
   a first sample processing apparatus;
   a second sample processing apparatus;
   a third sample processing apparatus;
   a variable deployment unit comprising:
   a first moving part comprising a rail, wherein the first moving part is configured to simultaneously move the second and third sample processing apparatuses relative to the first sample processing apparatus back and forth in a first direction via the rail;
   a second moving part comprising a rail connected with the first moving part, wherein the second moving part is configured to support the second sample processing apparatus and to move, via the rail of the second moving part, the second sample processing apparatus relative to the first moving part and to the first sample processing apparatus back and forth in a second direction that is substantially perpendicular to the first direction; and
   a third moving part comprising a rail connected with the first moving part, wherein the third moving part is configured to support the third sample processing apparatus and to move, via the rail of the third moving part, the third sample processing apparatus relative to the first moving part and to the first sample processing apparatus back and forth in the second direction,
   wherein the second moving part and third moving part are each further configured to respectively move the second sample processing apparatus and the third sample processing apparatus independent of the other in the second direction.

2. The sample processing system of claim 1, wherein the variable deployment unit further comprises:
   a first guide part for guiding the movement of the first moving part in the first direction via the rail of the first moving part; and
   a second guide part for guiding the movement of the second moving part in the second direction.

3. The sample processing system of claim 1, wherein the variable deployment unit further comprises:
   a third guide part for guiding the movement of the second moving part in the second direction via the rail of the second moving part;
   a fourth guide part for guiding the movement of the third moving part in the second direction via the rail of the third moving part; and a fifth guide part for guiding the movement of the third guide part and the fourth guide part in the first direction via the rail of the first moving part.

4. The sample processing system of claim 3, wherein the fifth guide part independently guides the movement of the third guide part and the fourth guide part in the first direction.

5. The sample processing system of claim 4, wherein the fifth guide part comprises:
a first movement path for guiding the movement of the third guide part in the first direction; and
a second movement path for guiding the movement of the fourth retaining part in the first direction.

6. The sample processing system of claim 1, wherein the second sample processing apparatus comprises a conveying apparatus for transporting a sample, which has been processed by the first sample processing apparatus, to the third sample processing apparatus.

7. The sample processing system of claim 1, wherein
the first sample processing apparatus comprises a sample preparing apparatus for preparing an analysis sample;
the second sample processing apparatus comprises a conveying apparatus for transporting the analysis sample prepared in the first sample processing apparatus to the third sample processing apparatus; and
the third sample processing apparatus comprises an analyzer for analyzing the analysis sample prepared in the first sample processing apparatus.

8. The sample processing system of claim 1, wherein the first sample processing apparatus, second sample processing apparatus, and third sample processing apparatus are deployed along a sample conveying line which extends in the first direction for supplying a sample to the first sample processing apparatus when the sample is to be processed.

9. The sample processing system of claim 1 further comprising a moving mechanism, wherein the moving mechanism independently moves the first sample processing apparatus in the second direction from a condition in which the first sample processing apparatus, second sample processing apparatus, and the third sample processing apparatus are lined up in the first direction.

10. The sample processing system of claim 1, wherein
the second sample processing apparatus is deployed adjacent to the first sample processing apparatus; and
the third sample processing apparatus is deployed adjacent to the second sample processing apparatus on the opposite side from the first sample processing apparatus so as to have the second sample processing apparatus interposed therebetween.

11. A sample processing system comprising:
a first sample processing apparatus;
a second sample processing apparatus;
a third sample processing apparatus;
a variable deployment unit comprising:
a first moving part comprising a rail, wherein the first moving part is configured to simultaneously move the second and third sample processing apparatuses relative to the first sample processing apparatus back and forth in a first direction via the rail;
a second moving part comprising a rail connected with the first moving part, wherein the second moving part is configured to support the second sample processing apparatus and to move, via the rail of the second moving part, the second sample processing apparatus relative to the first moving part and to the first sample processing apparatus back and forth in a second direction that is substantially perpendicular to the first direction; and a third moving part comprising a rail connected with the first moving part, wherein the third moving part is configured to support the third sample processing apparatus and to move, via the rail of the third moving part, the third sample processing apparatus relative to the first moving part and to the first sample processing apparatus back and forth in the second direction,
wherein the second moving part and third moving part are each further configured to respectively move the second sample processing apparatus and the third sample processing apparatus relative to the first sample processing apparatus in a first direction and in a second direction that crosses the first direction.

12. The sample processing system of claim 11, wherein the variable deployment unit comprises:
a first guide part for guiding the movement, in a first direction, of the first moving part; and
a second guide part for guiding the movement of the second moving part in the second direction.

13. The sample processing system of claim 11, wherein the variable deployment unit comprises:
a third guide part for guiding the movement of the second moving part in the second direction via the rail of the second moving part;
a fourth guide part for guiding the movement of the third moving part in the second direction via the rail of the third moving part; and
a fifth guide part for guiding the movement of the third guide part and the fourth guide part in the first direction via the rail of the first moving part.

14. A sample processing system comprising:
a first sample processing apparatus;
a second sample processing apparatus;
a variable deployment unit comprising:
a first moving part configured to simultaneously move the second sample processing apparatus relative to the first sample processing apparatus back and forth in a first direction;
a second moving part connected with the first moving part and configured to support the second sample processing apparatus and to move the second sample processing apparatus back and forth in both a first direction relative to the first sample processing apparatus and a second direction crossing the first direction.

15. The sample processing system of claim 1, wherein the variable deployment unit comprises a stationary part configured to remain at a fixed point relative to the first sample processing apparatus during movement of the second or a third sample processing apparatuses.

16. A sample processing system comprising:
a first sample processing apparatus;
a second sample processing apparatus;
a third sample processing apparatus;
a variable deployment unit comprising:
a first moving part configured to simultaneously move the second and third sample processing apparatuses relative to the first sample processing apparatus back and forth in a first direction;
a second moving part connected with the first moving part and configured to support the second and third sample processing apparatuses and to move the second and third sample processing apparatuses relative to the first moving part and to the first sample processing apparatus back and forth in a second direction substantially perpendicular to the first direction, and wherein the variable deployment unit is configured to:
  deploy, via the first and second moving parts, the second and third sample processing apparatuses into a first and a second deployment configuration relative to the first sample processing apparatus, wherein:
    according to the first deployment configuration the second sample processing apparatus is between the first and third sample processing apparatuses along a first axis, wherein the third sample processing apparatus is offset from the first sample processing apparatus along the first axis by at least a width of the second sample processing apparatus, and
    according to the second deployment configuration the second and third sample processing apparatuses are offset from the respective positions of the second and third sample processing apparatuses according to the first deployment configuration by a first distance along a second axis that is substantially perpendicular to the first axis.

17. The sample processing system of claim 16, wherein the variable deployment unit is further configured to deploy the second and third sample processing apparatuses into a third deployment configuration in which:
  the second sample processing apparatus is offset from the position of the second sample processing apparatus according to the first deployment configuration by the first distance along the second axis, and
  the third sample processing apparatus is offset from the position of the third sample processing apparatus according to the first deployment configuration by the first distance along the second axis and by a second distance along the first axis.

18. The sample processing system of claim 16, wherein the variable deployment unit is further configured to deploy the second and third sample processing apparatuses into a third deployment configuration in which the second and third sample processing apparatuses are offset from the respective positions of the second and third sample processing apparatuses according to the first deployment configuration by the first distance along the second axis and by a second distance along the first axis.

* * * * *